(12) United States Patent
Rajala

(10) Patent No.: US 6,527,902 B1
(45) Date of Patent: Mar. 4, 2003

(54) PROCESS AND APPARATUS FOR CUTTING OF DISCRETE COMPONENTS OF A MULTI-COMPONENT WORKPIECE AND DEPOSITING THEM WITH REGISTRATION ON A MOVING WEB OF MATERIAL

(75) Inventor: Gregory John Rajala, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 136 days.

(21) Appl. No.: 09/669,915

(22) Filed: Sep. 25, 2000

Related U.S. Application Data

(62) Division of application No. 09/088,354, filed on Jun. 1, 1998, now Pat. No. 6,165,306.

(51) Int. Cl.[7] .............................. B26D 5/00; B26F 1/38; A61F 13/15; B32B 31/00

(52) U.S. Cl. ..................... 156/263; 156/264; 156/265; 156/302; 156/303; 156/362; 156/511; 156/519; 156/552

(58) Field of Search ................................ 156/263, 265, 156/302, 303, 364, 324, 511, 519, 552, 358, 362, 363, 264, 378, 512, 522, 556; 83/26, 40, 50, 3; 604/385.01, 385.101, 385.14, 385.21, 385.23, 386

(56) References Cited

U.S. PATENT DOCUMENTS

| | | | |
|---|---|---|---|
| 2,254,217 A | 9/1941 | Grupe | 93/36.6 |
| 2,958,365 A | 11/1960 | Molins et al. | 154/36 |
| 3,139,243 A | 6/1964 | Warwick et al. | 242/156.2 |
| 3,146,152 A | 8/1964 | Seragnoli | 156/519 |
| 3,516,891 A | 6/1970 | Hubin | 156/521 |
| 3,537,934 A | 11/1970 | Munch | 156/364 |
| 3,582,437 A | 6/1971 | Lenk | 156/521 |
| 3,645,463 A | 2/1972 | Helm | 242/58.1 |
| 3,728,191 A | 4/1973 | Wierzba et al. | 156/265 |
| 3,746,599 A | 7/1973 | Peeters et al. | 156/505 |
| 3,758,367 A | 9/1973 | Berg | 156/519 |
| 3,835,756 A | 9/1974 | Bosse | 93/8 WA |
| 3,850,724 A | * 11/1974 | Lehmacher | 156/201 |
| 3,858,819 A | 1/1975 | Butler, Jr. | 242/58.3 |
| 3,879,246 A | 4/1975 | Walker | 156/265 |
| 3,886,031 A | 5/1975 | Taitel | 156/504 |
| 3,904,147 A | 9/1975 | Taitel et al. | 242/156.2 |
| 3,918,655 A | 11/1975 | Hillner et al. | 242/58.1 |
| 3,939,032 A | 2/1976 | Taitel et al. | 156/505 |
| 3,957,570 A | 5/1976 | Helm | 156/519 |
| 3,963,557 A | 6/1976 | Patterson | 156/519 |
| 3,995,791 A | 12/1976 | Schoppee | 242/58.1 |
| 4,010,911 A | 3/1977 | Heitmann | 242/58.4 |

(List continued on next page.)

FOREIGN PATENT DOCUMENTS

| | | | |
|---|---|---|---|
| EP | 0 677 378 A2 | 10/1995 | B31B/1/90 |
| EP | 0 692 375 A2 | 1/1996 | |
| FR | 2 203 358 | 5/1974 | B65C/9/00 |
| JP | 4-28363 | 1/1992 | A61F/13/54 |
| WO | 94/02402 | 2/1994 | B65H/39/14 |
| WO | 95/19752 | 7/1995 | A61F/13/15 |
| WO | 96/23470 | 8/1996 | |

OTHER PUBLICATIONS

US 4,909,885, 3/1990, Swenson (withdrawn)

*Primary Examiner*—Linda Gray
(74) *Attorney, Agent, or Firm*—Wilhelm Law Service; Thomas D. Wilhelm

(57) ABSTRACT

This invention pertains to a machine and process for cutting discrete workpiece components from webs of material, precisely registering them with respect to one another, and depositing them with precise registration onto a constantly moving web of material, the webs of material optionally all moving at different speeds. In a particular embodiment of the invention, a process for manufacturing a multi-component absorbent personal hygiene article is described.

12 Claims, 12 Drawing Sheets

U.S. PATENT DOCUMENTS

| | | | |
|---|---|---|---|
| 4,021,293 A | 5/1977 | Total | 156/568 |
| RE29,365 E | 8/1977 | Butler, Jr. | 242/58.3 |
| 4,045,275 A | 8/1977 | Stohlquist et al. | 156/521 |
| 4,061,527 A | 12/1977 | Traise | 156/519 |
| 4,083,737 A | 4/1978 | Foote, Jr. et al. | 156/73.1 |
| 4,120,739 A | 10/1978 | Peeters et al. | 156/506 |
| 4,157,934 A | 6/1979 | Ryan et al. | 156/504 |
| 4,190,475 A | 2/1980 | Marschke | 156/157 |
| 4,190,483 A | 2/1980 | Ryan et al. | 156/504 |
| 4,261,782 A | 4/1981 | Teed | 156/361 |
| 4,262,855 A | 4/1981 | Haag | 242/58.1 |
| 4,309,236 A | 1/1982 | Teed | 156/164 |
| 4,364,787 A | 12/1982 | Radzins | 156/164 |
| 4,371,417 A | 2/1983 | Frick et al. | 156/495 |
| 4,374,576 A | 2/1983 | Ryan | 242/58.4 |
| 4,394,898 A | 7/1983 | Campbell | 198/374 |
| 4,404,058 A | 9/1983 | Marchini | 156/571 |
| 4,443,291 A | 4/1984 | Reed | 156/504 |
| 4,455,190 A | 6/1984 | Bianchetto et al. | 156/504 |
| 4,481,053 A | 11/1984 | Tokuno et al. | 156/157 |
| 4,525,229 A | 6/1985 | Suzuki et al. | 156/161 |
| 4,572,043 A | 2/1986 | Bianco | 83/18 |
| 4,578,133 A | 3/1986 | Oshefsky et al. | 156/164 |
| 4,608,115 A | 8/1986 | Schroth et al. | 156/519 |
| 4,610,751 A | 9/1986 | Eschler | 156/517 |
| 4,617,082 A | 10/1986 | Oshefsky et al. | 156/447 |
| 4,645,554 A | 2/1987 | Wyser | 156/159 |
| 4,719,855 A | 1/1988 | Cannon et al. | 101/426 |
| 4,726,876 A | 2/1988 | Tomsovic, Jr. | 156/552 |
| 4,762,582 A | 8/1988 | de Jonckheere | 156/164 |
| 4,767,487 A | 8/1988 | Tomsovic, Jr. | 156/256 |
| 4,769,098 A | 9/1988 | Cederholm et al. | 156/159 |
| 4,776,911 A | 10/1988 | Uda et al. | 156/161 |
| 4,776,920 A | 10/1988 | Ryan | 156/504 |
| 4,786,346 A | 11/1988 | Ales et al. | 156/160 |
| 4,795,510 A | 1/1989 | Wittrock et al. | 156/64 |
| 4,801,342 A | 1/1989 | Wheeler et al. | 156/159 |
| 4,880,178 A | 11/1989 | Goulette | 242/58.1 |
| 4,923,546 A | 5/1990 | Wheeler et al. | 156/159 |
| 4,987,940 A | 1/1991 | Straub et al. | 156/164 |
| 4,995,936 A | 2/1991 | Cohn | 156/504 |
| 5,021,111 A | 6/1991 | Swenson | 156/264 |
| 5,030,311 A | 7/1991 | Michal et al. | 156/256 |
| 5,041,073 A | 8/1991 | Eicker | 493/377 |
| 5,066,346 A | 11/1991 | Long et al. | 156/157 |
| 5,091,039 A | 2/1992 | Ujimoto et al. | 156/519 |
| 5,102,485 A | 4/1992 | Keeler et al. | 156/256 |
| 5,102,486 A | 4/1992 | Midgley et al. | 156/256 |
| 5,122,216 A | 6/1992 | Goodwin, III | 156/303 |
| 5,127,981 A | 7/1992 | Straub et al. | 156/519 |
| 5,131,593 A | 7/1992 | Siegfried et al. | 242/58.1 |
| 5,200,020 A | 4/1993 | Collins et al. | 156/520 |
| 5,235,515 A | 8/1993 | Ungpiyakul et al. | 364/469 |
| 5,244,530 A | 9/1993 | Collins et al. | 156/519 |
| 5,261,996 A | 11/1993 | Rossini | 156/521 |
| 5,286,543 A | 2/1994 | Ungpiyakul et al. | 428/74 |
| 5,314,568 A | 5/1994 | Ryan | 156/504 |
| 5,380,381 A | 1/1995 | Otruba | 156/64 |
| 5,383,988 A | 1/1995 | Herrmann et al. | 156/64 |
| 5,407,507 A | 4/1995 | Ball | 156/163 |
| 5,407,513 A | 4/1995 | Hayden et al. | 156/265 |
| 5,413,651 A | 5/1995 | Otruba | 156/64 |
| 5,415,716 A | 5/1995 | Kendall | 156/256 |
| 5,492,591 A | 2/1996 | Herrmann et al. | 156/538 |
| 5,549,783 A | 8/1996 | Schroeder et al. | 156/542 |
| 5,552,007 A | 9/1996 | Rajala et al. | 156/164 |
| 5,556,504 A | 9/1996 | Rajala et al. | 156/519 |
| 5,562,793 A | 10/1996 | Menard | 156/263 |
| 5,580,411 A | 12/1996 | Nease et al. | 156/260 |
| 5,582,668 A | 12/1996 | Kling | 156/161 |
| 5,591,297 A | 1/1997 | Ahr | 156/521 |
| 5,595,335 A | 1/1997 | Borel | 226/42 |
| 5,597,437 A | 1/1997 | Lange et al. | 156/260 |
| 5,643,396 A | 7/1997 | Rajala et al. | 156/361 |
| 5,659,538 A | 8/1997 | Stuebe et al. | 364/469.02 |
| 5,660,657 A | 8/1997 | Rajala et al. | 156/64 |
| 5,679,195 A | 10/1997 | O'Dwyer et al. | 156/159 |
| 5,693,165 A | 12/1997 | Schmitz | 156/164 |
| 5,695,846 A | 12/1997 | Lange et al. | 428/98 |
| 5,702,551 A | 12/1997 | Huber et al. | 156/73.1 |
| 5,705,013 A | 1/1998 | Nease et al. | 156/260 |
| 5,716,478 A | 2/1998 | Boothe et al. | 156/302 |

* cited by examiner

PROCESS AND APPARATUS FOR CUTTING OF DISCRETE COMPONENTS OF A MULTI-COMPONENT WORKPIECE AND DEPOSITING THEM WITH REGISTRATION ON A MOVING WEB OF MATERIAL

CROSS-REFERENCE TO RELATED APPLICATIONS

This application is a Divisional application claiming priority under 35 U.S.C. 120 to application Ser. No. 09/088,354 filed Jul. 1, 1998, which is incorporated herein by reference in its entirety, now U.S. Pat. No. 6,165,306.

FIELD OF THE INVENTION

The present invention relates to a method and apparatus for receiving discrete parts of a workpiece traveling at different speeds relative to one another and applying the parts to a moving web of material. More particularly, the invention concerns a method and apparatus for receiving discrete parts from at least two webs of moving material moving at different speeds and depositing the discrete parts with controllable registration on a third continuously moving web of material.

BACKGROUND OF THE INVENTION

Articles such as infant diapers, adult continence diapers, feminine napkins and the like have been manufactured generally by processes where discrete parts or components of the article are deposited on a continuously moving product web. Often, the speed with which the parts or components are produced and fed into the process is not the same as the speed of advance of the product web itself. In such cases, the speed of production and/or deposition of the component parts on the moving web must be varied to match the speed of the product web to properly match the parts to the moving web without adversely affecting the process or finished article.

Several methods for changing the speed of a part or component of material for deposition on a continuously moving web are known in the art. One method employs rollers segmented into sections which are inwardly and outwardly moveable in a direction radial to their direction of rotation. As the roller rotates, the segments are driven by cam actuating or gearing means to move inwardly and outwardly changing the linear surface speed of the roller segments as the roller rotates through each revolution.

Another method utilizes festoons to reduce the speed of the moving web to which the parts or components are to be applied. The continuously moving web is temporarily slowed to the speed of the component parts to be deposited, with the excess portion of the continuously moving web gathering in festoons. While the continuously moving web is slowed to match the speed of the component parts, the parts are transferred to the web and the speed of the web is then accelerated to gather the festoons prior to the next cycle.

Another method is the so-called "slip gap" method in which the parts or components are cut from a web of material moving at a slower speed than the product web. As the component parts are cut from the first web of material, they are held to either the anvil roller or the cutter roller by means of vacuum. As the pieces pass tangentially to the continuously moving product web which is moving at a different speed, the parts or components slip temporarily until they are vacuum transferred to the continuously moving product web.

These known methods of transferring component parts, moving at one speed, to a continuously moving web moving at a different speed, do not address the problem of insuring careful registration of the deposited component parts on the continuously moving web. The problem is exacerbated when the need exists for depositing two or more components, one on top of the other on the continuously moving web while insuring careful registration of one component to the other, or to the moving web.

SUMMARY

In one embodiment, the present invention provides a process for manufacturing a multi-component workpiece comprising at least two components cut from moving webs of material, registering the components with respect to one another, and depositing the registered components with on a web of moving material. The process comprises the steps of a) cutting the first discrete workpiece components from a web of first material moving at first web speed, b) cutting the second discrete workpiece components from a web of second material moving at a second web speed, c) mating the first and second discrete workpiece components and registering them with respect to one another, and d) depositing the mated first and second workpiece components with registration on a third web of material moving at a third constant speed.

In another embodiment, the invention provides a machine for cutting first and second discrete workpiece components, respectively, from first and second webs of material running at different constant web speeds, the first and second workpiece components being optionally of different lengths, registering them with respect to one another, and depositing them with registration on a third web of material moving at a third constant web speed.

The machine comprises a first apparatus for cutting discrete components from a web of material moving at a first web speed, and a second apparatus for cutting discrete components of a second material from a web of second material moving at a second web speed. Speed matching apparatus comprises a first speed matching roller for receiving first discrete workpiece components from the first cutting apparatus and a second speed matching roller for receiving second discrete workpiece components from the second cutting apparatus, and mating and registering the first and second workpiece components with respect to one another and depositing them with registration on the third web of material moving at a third constant speed.

Non-constant drive means drives the first and second speed matching rollers independently, each at a higher constant dwell speed and a lower constant dwell speed with appropriate periods of acceleration and deceleration between the higher and lower constant dwell speeds. One of the higher or lower constant dwell speeds of the first speed matching roller matches the constant speed of the third web material, and the other of the higher or lower constant dwell speeds of the first speed matching roller matches the constant web speed of the first web material. One of the higher or lower constant dwell speeds of the second speed matching roller matches the constant speed of the first web material, and the other of the higher or lower constant dwell speeds of the second speed matching roller matches the constant web speed of the second web material.

In another embodiment, the present invention provides a method of manufacturing a multi-component absorbent personal hygiene article comprising a distribution or wicking component layer, a fluid transfer delay component layer, and an absorbent layer, deposited on a backing layer, the distribution, fluid retaining and absorbent layers being of different length and positionally registered with respect to one another on the backing layer.

BRIEF DESCRIPTION OF THE DRAWING FIGURES

Figure 1:
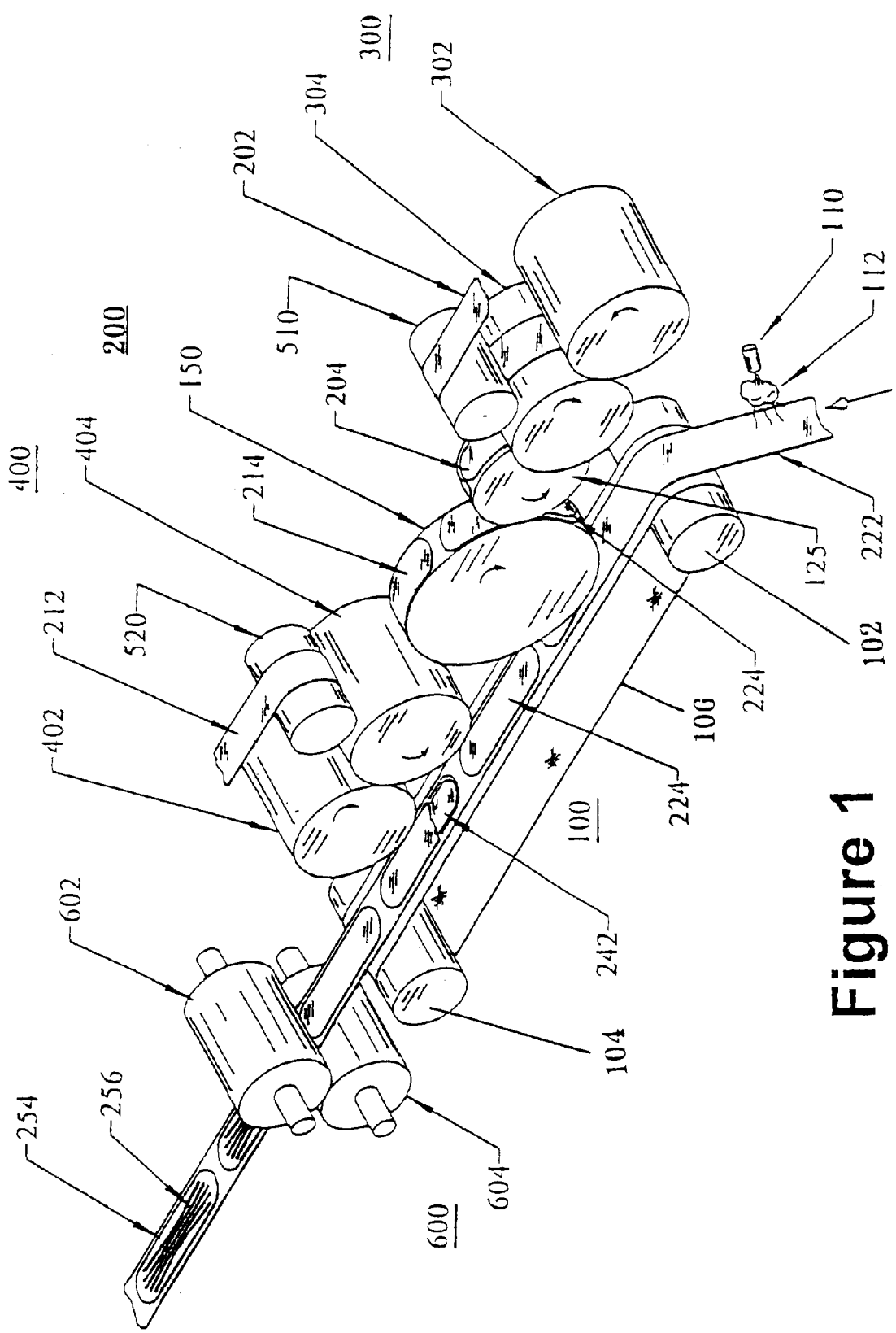
FIG. 1 shows, in a perspective view, a schematic representation of a machine in accordance with one embodiment of the invention.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals in the drawing figures are used to indicate like components.

DESCRIPTION OF THE ILLUSTRATED EMBODIMENTS

One embodiment of a machine in accordance with the present invention is represented in FIG. 1 which shows schematically a machine for depositing two components of differing lengths, cut from webs of material moving at different speeds, carefully registering them with respect to one another, and depositing them on a web moving at constant velocity. Since the two components have different lengths, the web from which each is cut and the apparatus for cutting each from that web, must move at different speeds. The machine of the invention provides for the mating and careful registration of the two components, as well as for the deposition of the mated components with careful registration on a web which is moving at a speed different from that of either of the two webs from which the components were cut.

The machine comprises as its main components, a web transport apparatus 100, a first component die cutting apparatus 400, a second component die cutting apparatus 300, component speed matching apparatus 200, and optional embossing apparatus 600. Rollers 102 and 104 of the web transport apparatus 100, 402 and 404 of the first component die cut apparatus 400, 302 and 304 of the second component die cut apparatus 300, and 602 and 604 of the optional embossing apparatus 600 are driven at constant speed equal to the machine line shaft speed, measured in terms of product per minute. Rollers 125 and 150 of the component speed matching apparatus 200 are driven at variable speed in the manner detailed below.

Referring to FIG. 1, a web 202 of a second material is delivered under slight tension to roller 510. The material then passes between anvil roller 302 and die cut roller 304 to cut the web 202 of second material into component pieces 204 having the desired shape and dimensions.

Figure 2:
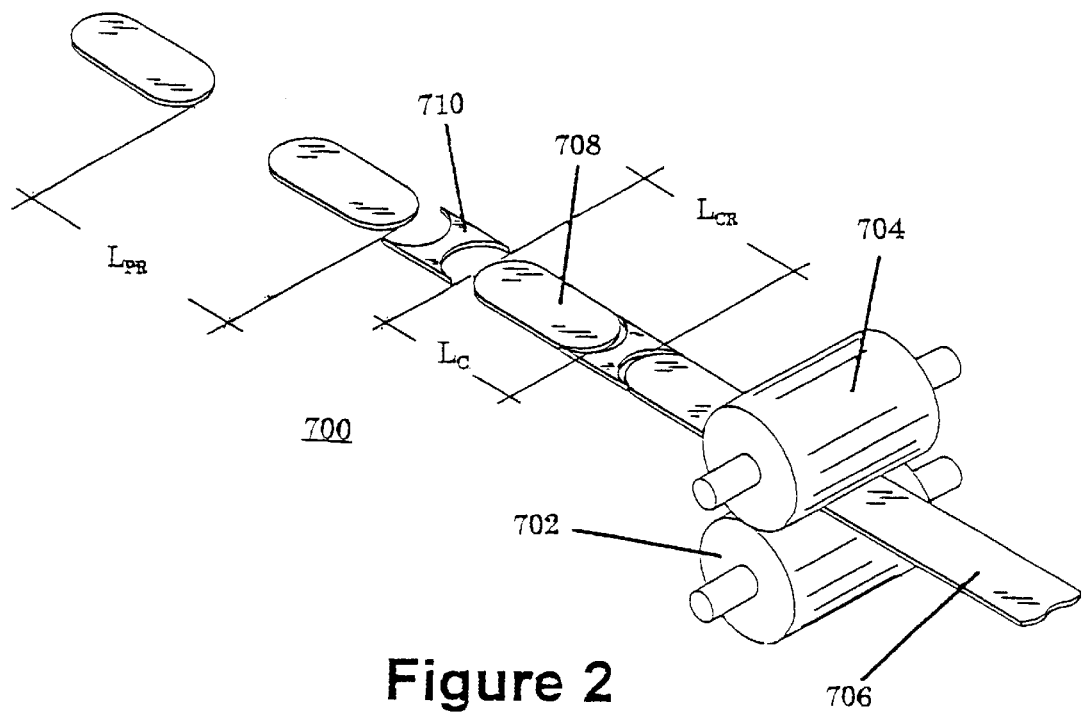
FIG. 2 shows a die cut and anvil roller assembly for cutting a web of material by the "butterfly cut" method.
Figure 3:
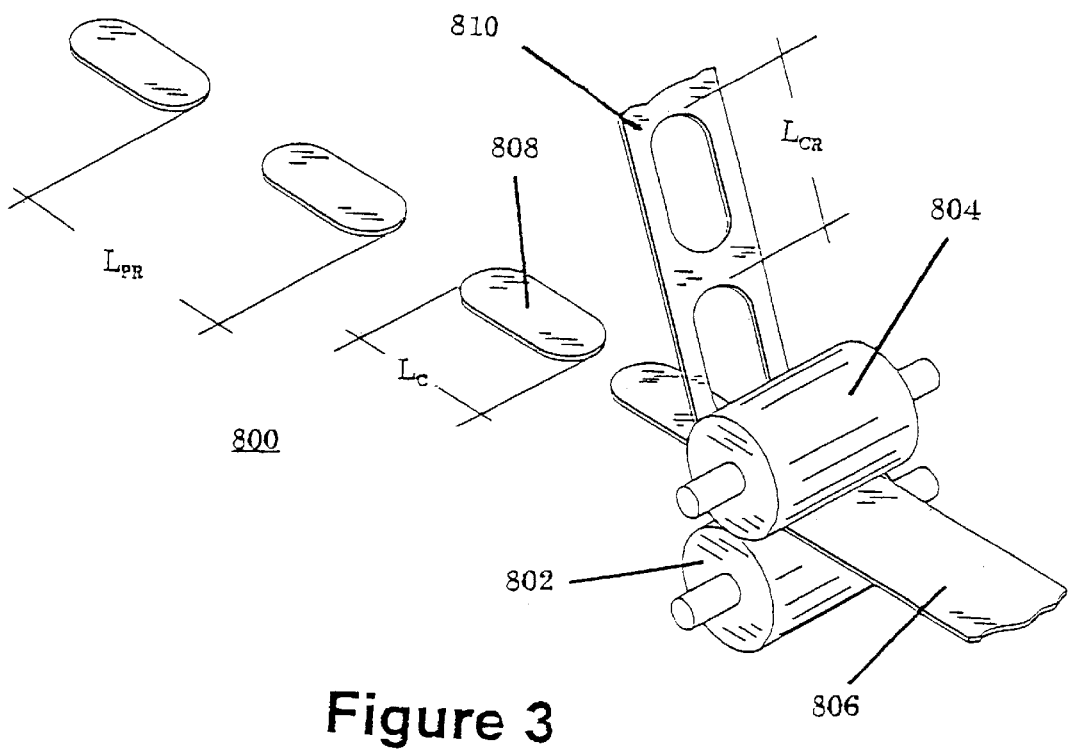
FIG. 3 shows a die cut and anvil roller assembly for cutting a web of material by the "ladder cut" method.

Die cutter 300 may be configured to cut component pieces by either a "butterfly cut" method or a "ladder cut" method as shown in FIGS. 2 and 3, respectively. The ladder cut method is depicted in ladder cut assembly 800 of FIG. 3, where an advancing web 806 of material passes between anvil roller 802 and die cut roller 804. The scrap "ladder" 810 of cut web is shown moving up and away from the die cut roller 804 and anvil roller 802. The cut component pieces 808 are shown moving along the process stream away from anvil roller 802 and die cut roller 804. The lengths of the cut component pieces 808 are indicated by the dimension $L_C$. The component repeat length, i.e. the distance between the leading edge of one cut component and the leading edge of the next following cut component, is indicated as $L_{CR}$ and the product repeat length, i.e. the distance between the leading edge of one completed workpiece and the leading edge of the next following workpiece in the product stream, is indicated at $L_{PR}$ which may or may not be the same as the component repeat lengths.

While shown as pieces having parallel sides and semi-circular ends, the component pieces 808, cut by the ladder cut method, may be of any desired shape. Since the web 806 of material is of a width greater than the width of the cut component pieces 808, there is a region of scrap in the ladder 810 along the sides of each component piece. Likewise, a scrap region of length $L_{CR}-L_C$ exists between successive component pieces. As a result, the component pieces 808 may be cut in any desired shape by the ladder cut method, as for example circular, elliptical, "dog-bone" shape, serrated, etc. While possessing the advantage of permitting the component pieces to be cut in any desired shape, the ladder cut method suffers, however, from the disadvantage of having more scrap than the butterfly cut method, which is depicted in FIG. 2.

In butterfly cut assembly 700 of FIG. 2, an advancing web 706 of material is shown as passing between anvil roller 702 and die cut roller 704 to produce the component pieces 708 cut by the butterfly method. The scrap pieces 710 are smaller than those derived from the ladder cut method. The component length, component repeat length, and product repeat length, are indicated as $L_C$, $L_{CR}$, and $L_{PR}$, respectively, as in FIG. 3.

Since, in the butterfly cut method, the web of material 706 is the same width as the final cut component pieces 708, there is less scrap but the cut pieces are constrained to have the parallel sides of the web 706. However, alternatively, the advancing web of material to be cut by the butterfly cut method may be previously cut so that the sides of the web have a repeating pattern of any desired shape. It is a simple matter to match the cutting frequency in the die cut roller to frequency of repetition of side-cut pattern in the web to produce component pieces cut by the butterfly cut method, but having shaped side edges. This alternative adds, however, to the cost and complexity of the process and the option of cutting component pieces from a web having parallel sides is preferred. The butterfly cut method is also preferred in those instances where the web of material to be cut into component pieces is costly, and the amount of scrap generated by the cutting process is to be minimized.

Referring again to FIG. 1, a web 212 of a first material is delivered under slight tension to roller 520. The material then passes between anvil roller 402 and die cut roller 404 to cut the web 212 of first material into first discrete workpiece components 214 having the desired shape and dimensions. Again, as discussed above, the workpiece components 214 may be cut from web 212 by either the ladder cut or butterfly cut method, as desired.

The first discrete workpiece components 214, traveling under essentially no tension, are held to the surface of die cut roller 404 by vacuum means discussed further below. Similarly, the discrete second workpiece components 204, traveling under essentially no tension, are held to the surface of die cut roller 304 by vacuum means.

Figure 4:
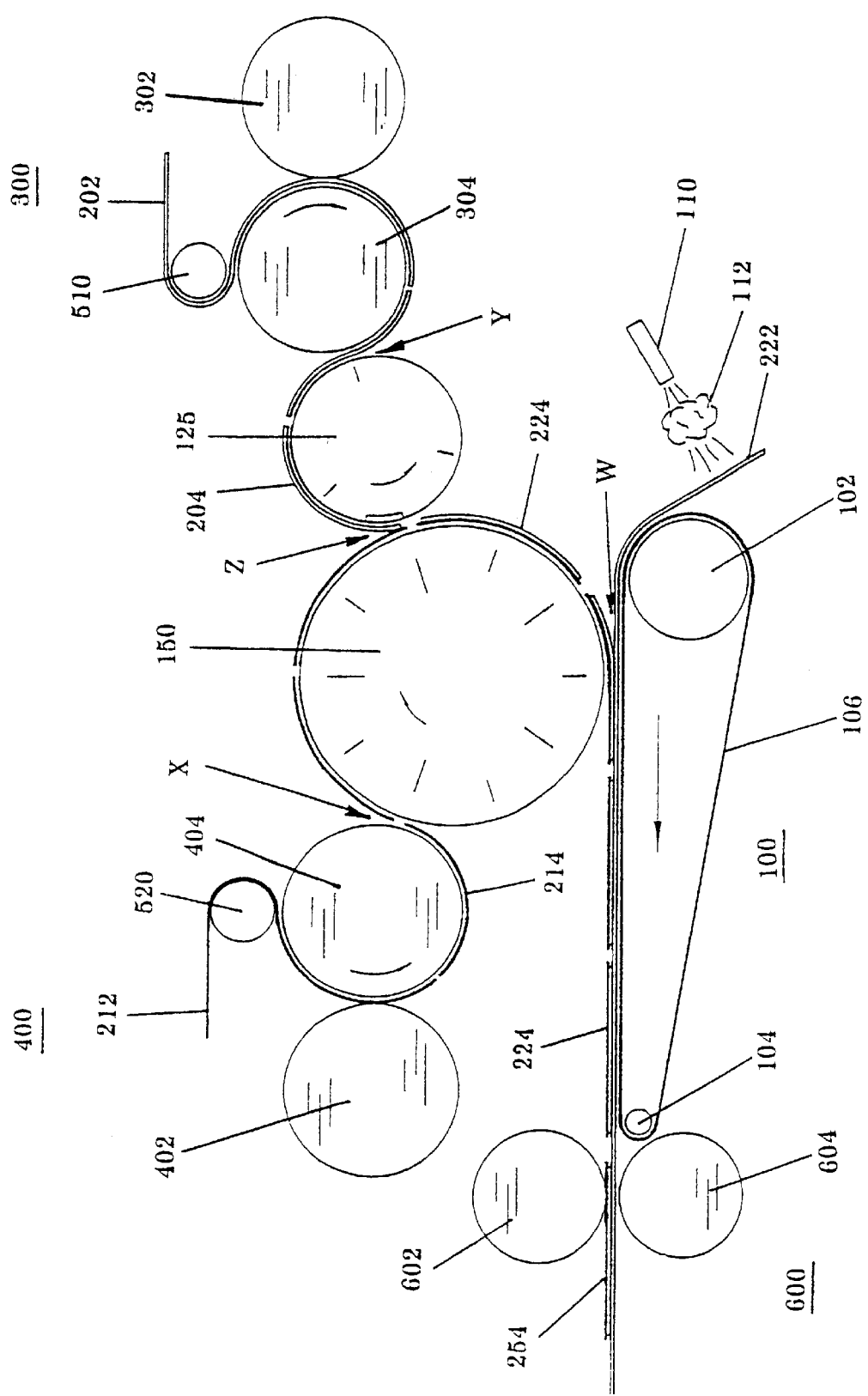
FIGS. 4 and 4A show a schematic partial side views of the machine depicted in FIG. 1.

Discrete first workpiece components 214 travel with die cut roller 404 until they enter the gap X between die cut roller 404 and speed matching roller 150 as shown in FIG. 4. This gap X is at least equal to the uncompressed thickness of web 212 of the first material. As a component 214 enters gap X, vacuum is released on die cut roller 404 and applied to speed matching roller 150 causing the component pieces 214 to transfer from die cut roller 404 to speed matching roller 150. Similarly, discrete second workpiece components 204 travel with die cut roller 304 until they enter the gap Y between die cut roller 304 and speed matching roller 125. This gap Y is at least equal to the uncompressed thickness of web 202 of the second material. Vacuum is released on die cut roller 304 and applied to speed matching roller 125 causing the cut pieces 204 to transfer from die cut roller 304 to speed matching roller 125.

As discrete first and second component pieces 214 and 204, move respectively with contra-rotating speed matching rollers 125 and 150 and enter gap Z between the first 150 and second 125 speed matching rollers, they are mated. The gap Z is at least equal to the combined uncompressed thicknesses of the web 212 of first material and the web 202 of second material. The vacuum holding second component piece 204 to speed matching roller 125 is released from speed matching roller 125, and second component piece 204 is transferred to speed transfer roller 150 by a higher vacuum which is turned on in speed matching roller 150 to hold both the first 214 and second 204 workpiece components to the roller 150. The first component 214, now sandwiched between second component 204 and the surface of speed matching roller 150, and component 214 are both held by vacuum to speed matching roller 150.

By indexing the die cut rollers 304 or 404 with respect to one another, the first component piece 214 can be controllably registered with respect to the second component piece 204 so that the first piece is centered on the second, or, in such a manner that the leading end of the advancing first piece leads or trails the leading edge of the second piece by any desired amount. This indexing is achieved in a manner well understood in the mechanical arts such as interposing between the machine line shaft and the shaft driving either or both die cut roller 304 or 404 a phase shift differential of the type manufactured by Fairchild Industrial Products Co., 1501 Fairchild Drive, Winston-Salem, N.C., USA under the trade name SPECON mechanical transmissions. This permits adjusting the phase angle between die cut rollers 304 and 404 to advance or delay the cutting of one of the components 204 or 214 with respect to the other.

Referring still to FIG. 1, a web 222 of a third material is fed under light tension from a roll of material, not shown, to web transport apparatus 100 which comprises rollers 102 and 104 and endless belt 106 passing over the rollers. The web 222 is held by conventional vacuum means, not shown, to the surface of the endless belt 106 which moves in the direction shown by the arrow.

As matched or mated first and second discrete component pieces, shown as 224 in FIGS. 1 and 4, continue to travel with speed matching roller 150, they enter gap W (FIG. 4) and meet the advancing web 222 and are transferred by releasing the vacuum which previously held the mated pair 224 to speed matching roller 150. The vacuum, applied to endless belt 106 causes the two pieces, still mated and registered in their positions relative to one another, to transfer to web 222 thereby to create a web assembly 254. Optionally, an adhesive, 112, applied to the web 222 by spray or slot coat applicator 110 serves to further bind the mated first and second component pieces 224 to the advancing web 222.

The mated pair 224, after transfer to the moving web 222, is also partially shown as a cutaway 242 in FIG. 1.

Optional further operations are applied to the workpieces as they advance through the machine, such as embossing overlying mated first and second components 224 with a pattern 256 by means of patterned embossing roller 602 and anvil roller 604 to produce an embossed workpiece 254, and applying further components to the workpiece in subsequent operations. It should be noted, however, that in the instance where a pattern 256 is to be embossed on web 222 and the overlying components 224, close registration of the components and the embossed pattern must also be maintained. This is accomplished by the machine of the invention by the close registration of the components making up 224 and the firm adherence of components 224 to the moving web 222.

Die cut apparatuses 300 and 400, embosser apparatus 600 rollers 510 and 520 are all driven from a common line shaft using conventional pulleys and gearboxes. The die cutting apparatuses 300 and 400 and embossing apparatus 600 perform one function with each revolution of the line shaft, while the receiving web transport 100 and rollers 510 and 520 advance the various webs passing respectively over them one product repeat length with each revolution of the line shaft. In contrast, the speed matching rollers 125 and 150 move at non-linear speeds during portions of each revolution in a manner which is described in detail below.

Having described the overall operation of the machine of the invention, the specifics of operation of the speed matching rollers 125 and 150 will now be described. Reference is made to FIG. 4 which shows a side view of the machine elements of FIG. 1. Identical reference numerals are used to denote the same elements in both FIGS. 1 and 4.

Roller 520, anvil roller 402 and die cut roller 404 are driven at a constant surface speed equal to the constant speed of material 212 through the first component die cut apparatus 400, that is, at a speed of $L_{CR1}$, per repeat where $L_{CR1}$ is the component repeat length of first workpiece component 214. (Workpiece speed expressed as repeat length per repeat is a convenient unit of workpiece speed since it is independent of the actual machine speed.) As the leading ends of each discrete component piece 214 approach the point of narrowest gap X between die cut roller 404 and speed matching roller 150, speed matching roller 150 decelerates to move with a surface speed equal to the surface speed of die cut roller 404. Speed matching roller 150 remains at this speed for a fraction f of workpiece repeat for the discrete component piece 214. This fraction of a repeat, f, is typically selected to provide sufficient time to turn off the vacuum holding first workpiece component 214 to die cut roller 404 and to turn on the vacuum which holds component 214 to speed matching roller 150. The length of the leading end of component 214 which advances during the period f is released from die cut roller 404 and transferred to speed matching roller 150 by the vacuum now applied to speed matching roller 150.

The length of time corresponding to f is chosen to be generally greater than one-tenth repeat. If the fraction of a repeat is too small, the time is too short to effectively turn the two vacuum controls off and on, and the fraction of the length of the workpiece component transferred to and held by the receiving roller is too short to insure effective transfer. Preferably f is from about 0.2 to about 0.4 repeat, most preferably of a value of about 0.25 for reasons which will be elaborated upon below.

After the length of component 214 corresponding to the fraction of repeat f has been transferred to speed matching roller 150, and the vacuum which formerly held the component 214 to die cut roller 404 has been turned off, the speed matching roller accelerates to match that of the web 222 to which the two components 204 and 214 are eventually transferred, i.e. a speed of $L_{PR}$ per repeat where $L_{PR}$ is the final product repeat length, and speed with which web 222 is moving.

Simultaneous with this course of events, a web of second material 202 passes over roller 510 and between anvil roller 302 and die cut roller 304 to cut the web 202 into discrete second workpiece components 204. Roller 510, anvil roller 302 and die cut roller 304 are driven at a constant surface speed equal to the constant speed of material 202 through the first component die cut apparatus 300, i.e. at a speed of $L_{CR2}$ per repeat where $L_{CR2}$ is the component repeat length of component 204. As the leading end of each discrete component piece 204 approaches the point of narrowest gap Y between die cut roller 304 and speed matching roller 125, speed matching roller 125 decelerates to a surface speed equal to the surface speed of die cut roller 304, i.e. $L_{C2}$ per repeat. Speed matching roller 125 remains at this speed for a fraction f of a repeat for the discrete component piece 204 to permit the transfer of a leading fraction of the length of second workpiece component 204 from die cut roller 304 to the speed matching roller 125. This is done in the manner described above, that is, by turning off the vacuum which holds component 204 to die cut roller 304 and turning on the vacuum which holds component 204 to speed matching roller 125.

Speed matching roller 125 then accelerates to match the speed of speed match roller 150, i.e. $L_{CR1}$ per repeat. As the leading ends of both first 204 and second 214 components approach the narrowest gap Z between speed matching rollers 125 and 150, the vacuum holding component 204 is turned off and a higher vacuum is applied to speed matching roller 150 and, as a consequence, component 204 is transferred to speed roller 150, sandwiching component 214 between component 204 and the surface of speed matching roller 150.

As the leading end of sandwiched components 204 and 214, designated 224 in FIG. 4, approach the point of narrowest gap W between speed matching roller 150 and endless belt 106 carrying web 222, speed matching roller 150 accelerates to match the speed of endless belt 106 and product web 222, i.e. a speed of $L_{PR}$ per repeat. The vacuum holding the sandwiched pair of components 224 to speed matching roller 150 is turned off and the continuous vacuum applied to endless belt 106 serves to transfer and hold the sandwiched or "stacked" pair of components 224 to endless belt 106. In addition, an adhesive 112, optionally applied to web 222 by spray or slot coat application 110 also serves to hold the bottom element of the sandwiched pair 224 to the web 222.

Having described generally the functioning of the speed matching rollers 125 and 150, their operation is explained in greater detail by reference to FIG. 5 which shows an enlarged segment of FIG. 4.

Figure 5:
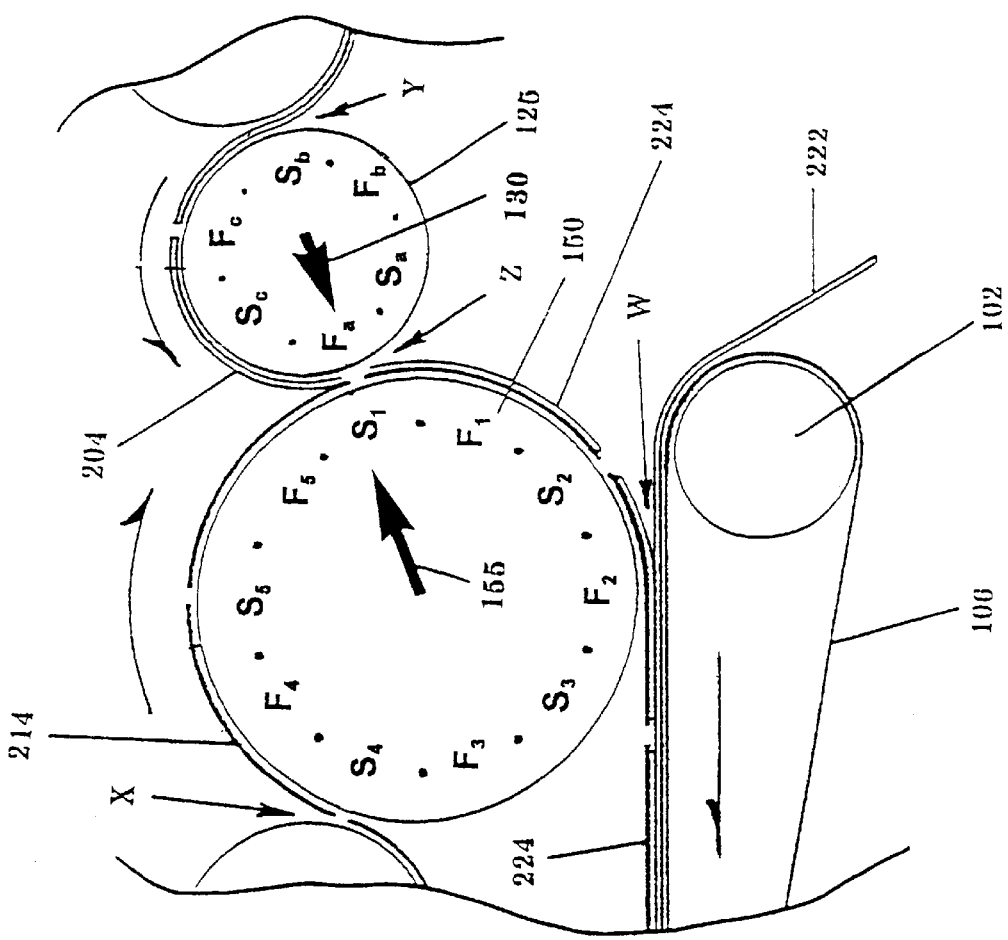
FIG. 5 shows an enlarged portion of the side view of the machine of FIG. 4.

In FIG. 5, speed matching rollers 125, 150, and endless belt 106 are shown with the directions of motion of each indicated by half-headed arrows. Speed matching roller 125 is driven by non-linear drive means described in more detail below, to move at a faster speed which is equal to the first component workpiece 214 repeat length per repeat, i.e $L_{CR1}$ per repeat, and at a slower speed which is equal to the second component repeat length per repeat, i.e. $L_{CR2}$ per repeat. The non-linear drive means appropriately accelerates and decelerates speed matching roller 125 between these second speed matching roller higher and lower speeds.

Similarly, speed matching roller 150 is driven by non-linear drive means to move at a first speed matching roller fast speed which is equal to the speed of the product web 222, that is at a speed of the product repeat length per repeat, $L_{PR}$ per repeat and at a slower speed which is equal to the higher speed of second speed matching roller 125, i.e. $L_{CR2}$ per repeat.

In FIG. 5, a first workpiece component 214 is shown entering the point of narrowest gap Z between speed roller 150 and speed roller 125 just as a second workpiece component 204 is likewise entering gap Z. The radial marking arrow 155 on speed matching roller 150 points to "$S_1$," indicating that, at this point in time, roller 150 is starting its dwell at the slower speed $L_{CR1}$ per repeat. As mentioned above, speed matching roller 150 dwells at this constant lower speed for a period f until the roller has turned in the direction of the arrow to the point where radial marking arrow 155 now points to the dot between "S1" and "F1." As speed matching roller 150 continues to rotate, the non-linear drive means accelerates the first speed matching roller 150 until the radial arrow 155 points to the marker "$F_1$". As roller 150 continues to rotate in the direction of the arrow, the non-linear drive means causes first speed matching roller to dwell at the higher speed, $L_{PR}$ per repeat, for the duration of rotation between "F1" and the dot between "F1" and "S2." As roller 150 continues to rotate, the non-linear drive means decelerates the roller until the radial arrow 155 points to $S_2$. Thus as the machine runs, first speed matching roller 150 dwells at high speed $L_{PR}$ per repeat, decelerates, dwells at low speed $L_{CR2}$ per repeat, and accelerates, in a repetitive or cyclical manner.

In the same manner, second speed matching roller 125 undergoes cyclical or repetitive dwells at constant higher speed $L_{CR1}$ per repeat, designated "$F_a$," "$F_b$," and "$F_c$," in FIG. 5, and constant slower speed dwells of $L_{CR2}$ per repeat, designated "$S_a$", "$S_b$", and "$S_c$," with appropriate periods of acceleration and deceleration between.

FIG. 5 shows speed matching rollers 125 and 150 in a position where radial arrow 155 on speed matching roller 150 points to the start of slower speed dwell $S_1$ for first speed matching roller 150. Radial arrow 130 on second speed matching roller 125, is pointing to the start of high speed dwell $F_a$ for second speed matching roller 125. As the rollers turn in the direction indicated by the half-headed arrows, radial arrow 155 on speed matching roller 150 will point to the dot between "S1" and "F1" indicating the start of acceleration of speed matching roller 150. During this period, speed matching roller 125 has turned so that radial arrow 130 now points to the dot between "Fa" and "Sa" indicating the start of deceleration of speed matching roller 125. At this point in time, a mismatch of speeds exists between speed matching rollers 125 and 150. This mismatch of speeds is made possible by the fact rollers 150 and 125 are not in contact, but have a gap, Z, between them. This gap is chosen to be at least equal to the combined uncompressed thicknesses of the two stacked workpiece components 204 and 214. In other words, rollers 125 and 150 are not nip rollers, applying pressure to the components to draw them through gap Z. The movement of the workpiece components is controlled, instead, by their being held to a particular roller by vacuum methods described above and detailed more fully below.

Workpiece component 214 is being held to roller 150 by vacuum, while the leading end of workpiece component 204 is being transferred to roller 150 by the vacuum applied to roller 150, the vacuum previously holding workpiece component 204 to roller 125 having been turned off. In this manner, workpiece component 204 is literally pulled slideably off roller 125, the trailing portion of the component 204 sliding across the surface of roller 125. This action has the advantage that workpiece 204 cannot "bunch up" on roller 150 during the transfer of the component from roller 125 to roller 150 which would be the consequence if the relative high and low speeds of the two rollers were reversed.

Figure 6:
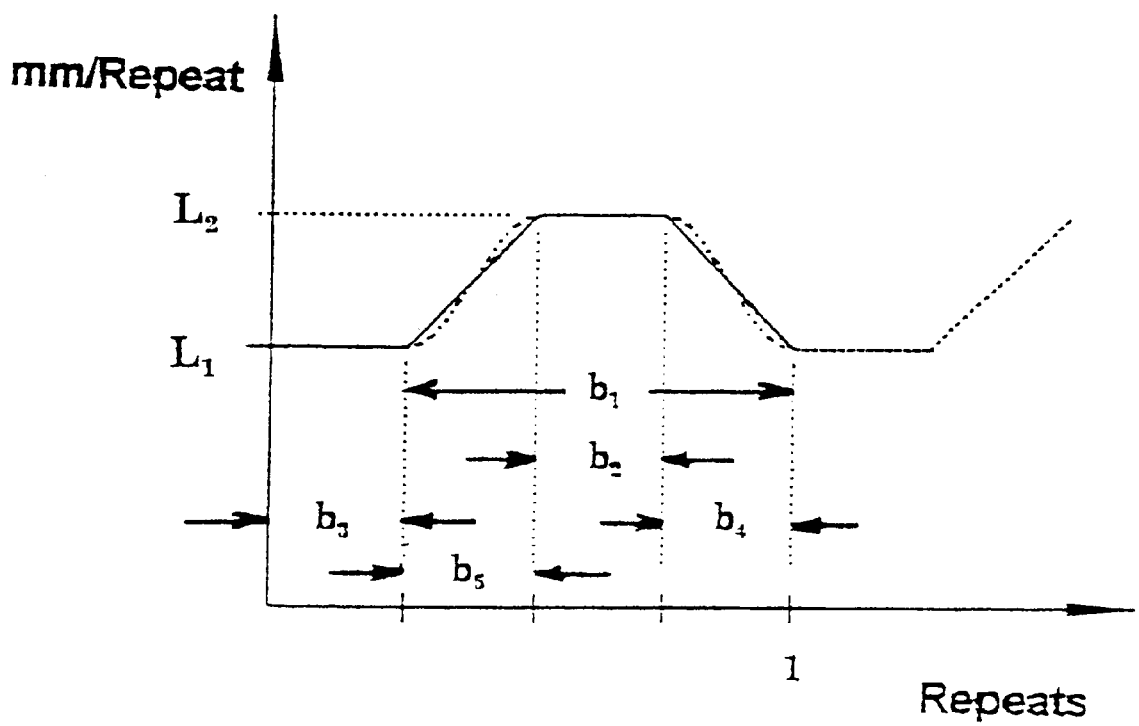
FIG. 6 shows a generalized speed profile diagram for non-linear drive gears for one embodiment of a machine of the invention.

First speed matching roller 150 is shown in the embodiment illustrated in FIGS. 1, 4 and 5 as having a circumference equal to five times the length corresponding to the area under speed profile curve for roller 150. (A generalized speed profile curve is shown in FIG. 6, and will be discussed further below.) Second speed matching roller 125 has a circumference equal to three times the area under the speed profile curve for roller 125. The circumference of either roller can independently take on any integral multiple value, n, of the area under its speed profile curve, although as a practical matter, not all values are feasible. Depending upon the length of the workpiece component, of course, speed matching rollers having a value of n=1 may be of too small a diameter to easily accommodate the required vacuum elements internal to the roller. However, in those instances where the workpiece repeat length is appreciable, rollers having a circumference corresponding to n=1 may be feasible.

At the opposite extreme, rollers which have circumferences equal to a large integral multiple of the workpiece component become so large and massive that their continual acceleration and deceleration between their slower and faster dwell speeds at high machine rates places strain on their non-linear drive systems.

A generalized speed profile curve is depicted in FIG. 6. The discussion of the generalized speed profile curve shown in FIG. 6 which follows will be to speed matching roller 150 for purposes of illustration. The higher speed $L_2$ of FIG. 6 is specifically $L_{PR}$ per repeat for the final workpiece. The lower speed, designated $L_1$ in FIG. 6, is $L_{CR1}$ per repeat for workpiece component 214. The sloping portions of the curve $b_4$ and $b_5$ represent, respectively, the deceleration and acceleration portions of the speed profile for roller 150. As indicated by the dotted line, the actual acceleration and deceleration portions of the speed curve are not linear, but the area under the curve is equal to that bounded by the heavier solid straight lines. The area under this curve, for speed matching roller 150 then becomes simply the sum of the rectangular area bounded by the line $L_1$ and 1 repeat, plus the area under the trapezoidal region of the speed curve bounded by the speed curve and L1. If the slow and fast speed dwell times, $b_3$ and $b_2$, respectively, and the acceleration and deceleration times $b_5$ and $b_4$, respectively, are chosen to be all equal, that is all 0.25 repeats, the area under the speed curve becomes simply the average of $L_2$ and $L_1$ or, specifically for roller 150, $(L_{PR}+L_{CR1})/2$. This is the distance swept by roller 150 in one product repeat cycle.

Given this distance, the circumference (and diameter) of roller 150 can be determined with a given choice for the value n, mentioned above. That is, speed matching roller 150 can be constructed with a circumference $n(L_{PR}+L_{CR1})/2$.

Similarly, in applying the generalized speed profile curve of FIG. 6 to speed matching roller 125, and using the analysis just presented for roller 150, the circumference of speed matching roller 125 becomes simply $n(L_{CR1}+L_{CR2})/2$.

Having discussed in detail the functioning of the speed matching rollers, there follows a discussion of the nature of the non-linear drive system for speed matching rollers 125 and 150.

Figure 8:
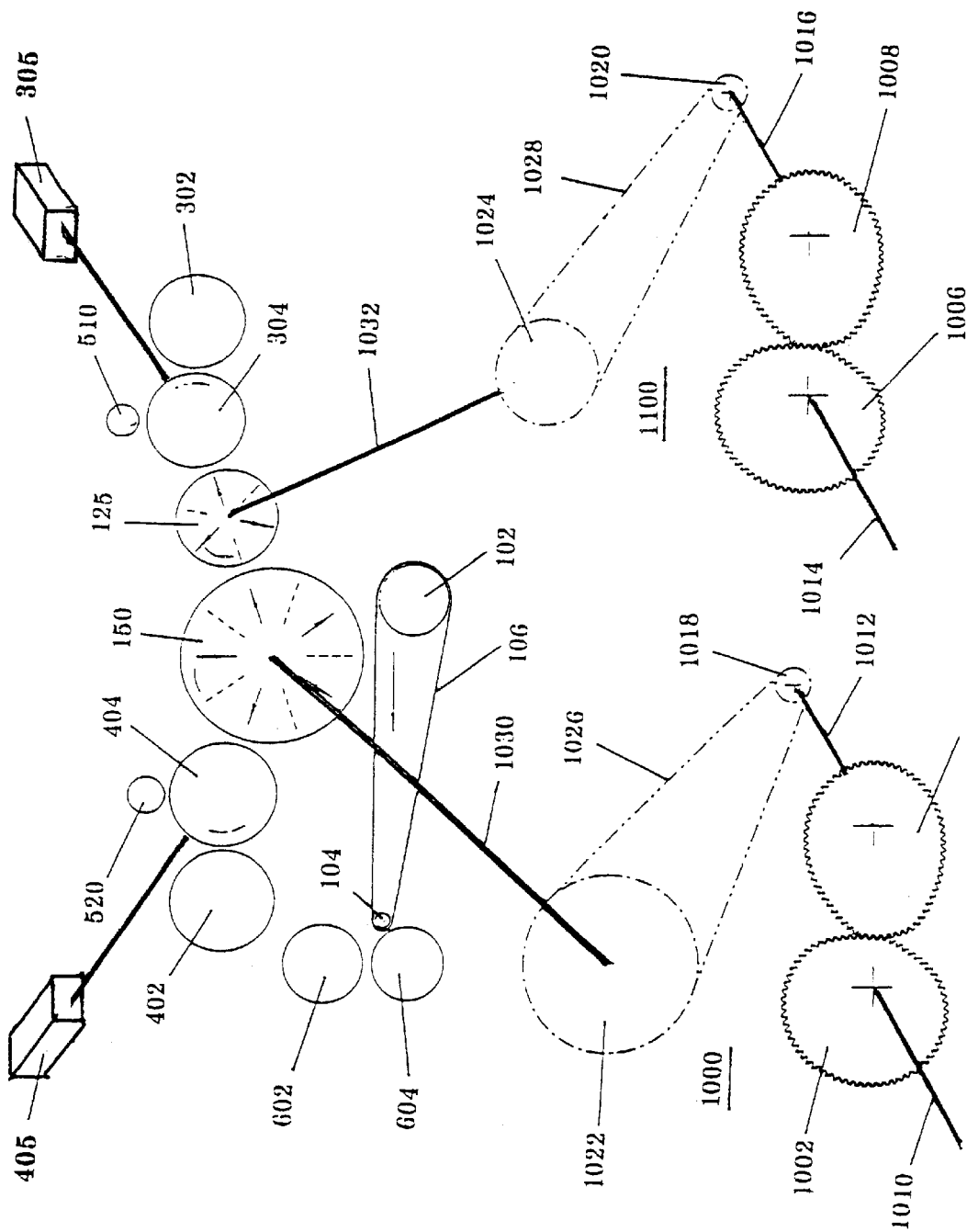
FIG. 8 is a schematic representation of the drive train for a machine of the invention.

The drives and linkages for one embodiment of a machine of the present invention are depicted in FIG. 8. Corresponding components in FIGS. 1, 4, 5 and 8 are given the same reference numbers for clarity.

A variety of means can be used to drive speed matching rollers 125 and 150 in a non-linear manner, including electronically controlled servo-motors, cam-and-follower mechanisms, and non-circular gear systems. The drive system must be capable, however, of standing up to the demanding work cycle. Non-circular gear drives are preferred because of their ruggedness and long mean-time-between failure rates compared with servo-motor systems and cam-and-follower mechanisms.

The use of an independent non-circular gear drive for each speed matching rollers 125 and 150 in the embodiment of the machine illustrated in the drawing figures thus provides an inexpensive and adaptable method for driving the two speed matching rollers.

The non-circular gear drive for each speed matching roller comprises a pair of gears: a non-circular input (drive) gear and a non-circular output (driven) gear. In each case the input gear is driven by the machine line shaft at a constant rate. To provide the variable angular velocities required by the speed matching rollers, the radius of the non-circular drive or input gear varies. Moreover, since the center-to-center distance between the non-circular gears remains constant, the radius of the non-circular driven or output gear changes to correspond to the changes in radius of the non-circular input or drive gear so that the two gears remain engaged or meshed during rotation.

The respective designs of the input or drive and output or driven non-circular gears are chosen to obtain the desired output function, for example, the speed profile for a typical speed matching roller as represented in FIG. 6, discussed above.

Non-circular gears, such as those employed in the machine and process of the present invention, can be purchased from Cunningham Industries, Inc. located in Stamford, Conn., USA. Alternatively, one of ordinary skill in the mechanical engineering art can fabricate the desired set of complementary non-circular gears, provided the analytical representation of the desired output function.

Figure 7:
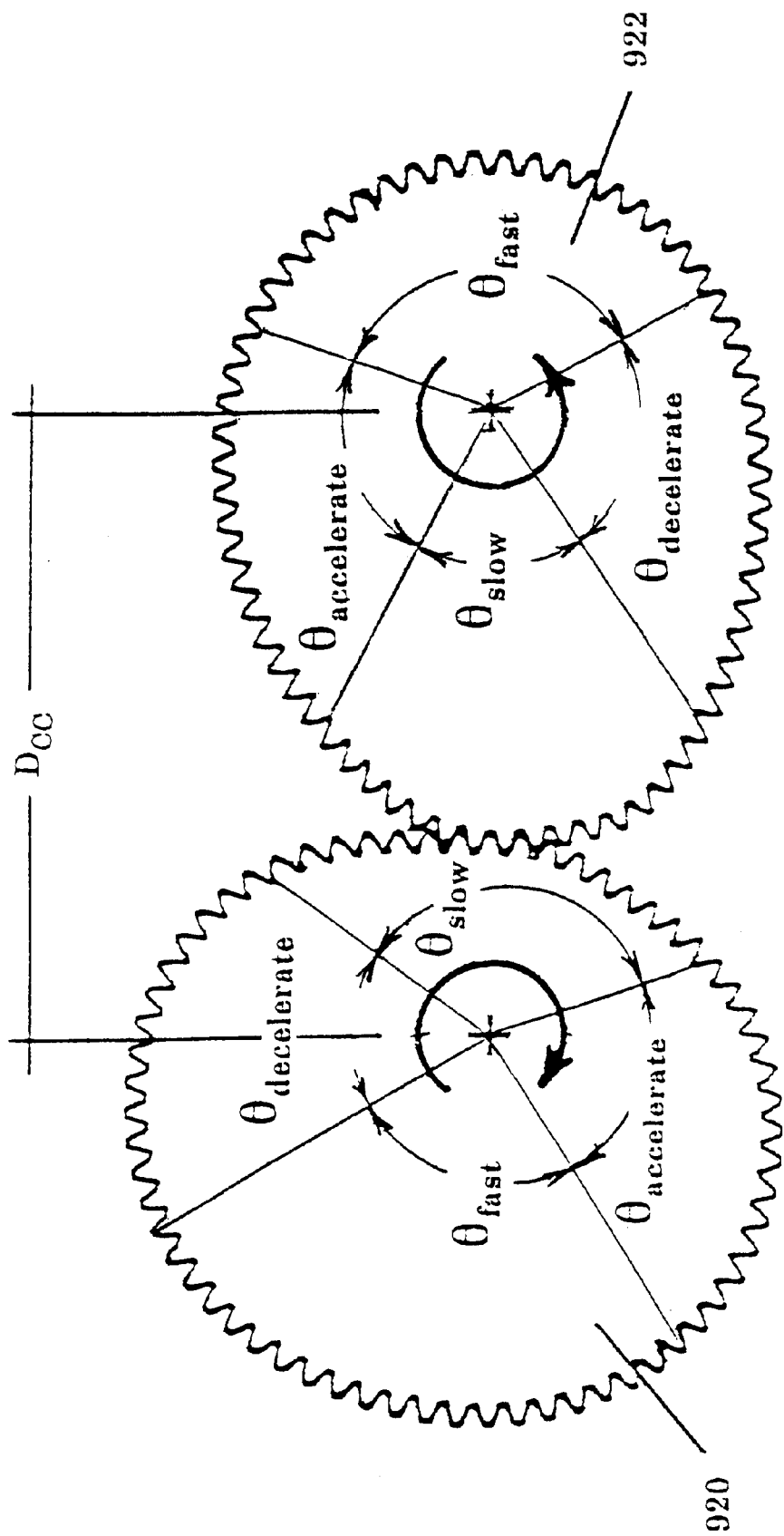
FIG. 7 is a generalized view of non-circular gears.

For example, the design of a set of non-circular gears, as representatively shown in FIG. 7, is developed as follows. First the output function, including the required process speeds and dwells is laid out, as illustrated in FIG. 6 to determine the proper radius of the orbital path taken by the speed matching rollers. Second, the coefficients which establish the transition or acceleration/deceleration portions of the non-circular gears is computed. Once the angles, ratios, and coefficients are known, the gear center-to-center distance is chosen which follows the required radii for the non-circular gears.

The radius, R, of the orbital path is determined by first calculating the total area under the output function curve illustrated in FIG. 6:

$$\text{Area} = L_1 + 0.5(b_1 + b_2)(L_2 - L_1) \quad \text{(Eqn. 1)}$$

$$R = \text{Area}/2\pi \quad \text{(Eqn. 2)}$$

where

R=the radius of the orbital path (mm)

Area=Area under the output function curve $L_1$=The low speed of the speed matching roller driven by the output gear (i.e. the mm/repeat for the component being transferred)

$L_2$=The high speed of the speed matching roller driven by the output gear (i.e. the mm/repeat for the product).

$b_1$=Total time (repeats) during the trapezoidal portion of the output function curve $b_2$=Total dwell time (repeats) at the high speed $b_3$=Total dwell time (repeats) at the low speed.

Once the radius of the orbital path is determined, the ratios and gear angles for the non-circular gears are determined as follows, where the input gear is shown as 920 and the output gear as 922 in FIG. 7:

$$\theta_{SLOW} \text{ for the input (drive) gear} = 2\pi b_3 \quad \text{(Eqn. 3)}$$

$$\theta_{FAST} \text{ for the input (drive) gear} = 2\pi b_2 \quad \text{(Eqn. 4)}$$

$$\theta_{ACCELERATE} \text{ for the input (drive) gear} = 2\pi(b_5 - b_2) \quad \text{(Eqn. 5)}$$

$$\theta_{DECELERATE} \text{ for the input (drive) gear} = 2\pi - (\theta_{SLOW} + \theta_{FAST} + \theta_{ACCELERATE}) \quad \text{(Eqn. 6)}$$

$$\theta_{SLOW} \text{ for the output (driven) gear} = (L_1 b_3)/R \quad \text{(Eqn. 7)}$$

$$\theta_{FAST} \text{ for the output (driven) gear} = (L_2 b_2)/R \quad \text{(Eqn. 8)}$$

$$\theta_{ACCELERATE} \text{ for the output (driven) gear} = [2b_5(L_1/2 + (L_2 - L_1)/4)]/R \quad \text{Eqn. 9}$$

$$\theta_{DECELERATE} \text{ for the output (drive) gear} = 2\pi - (\theta_{SLOW} + \theta_{FAST} + \theta_{ACCELERATE}) \quad \text{(Eqn. 10)}$$

Slow speed ratio=$Y_1$=($\theta_{SLOW}$ for the output gear)/($\theta_{SLOW}$ for the input gear)=$L_1/2\pi R$ (Eqn. 11)

High speed ratio=$Y_2$=($\theta_{FAST}$ for the output gear)/($\theta_{FAST}$ for the input gear)=$L_2/2\pi R$ (Eqn. 12)

Once the proper gear ratios and gear angles have been determined, the coefficients which define the shape of the non-circular gears can be computed. The segments of the peripheries of the input (drive) and output (driven) gears defined by the gear angles $\theta_{SLOW}$ and $\theta_{FAST}$ in each case will define the arc of a circle to insure that the slow and fast dwell times will be of constant speed. However, the segments of the peripheries of the input and output gears for the transition regions defined by the gear angles $\theta_{ACCELERATE}$ and $\theta_{DECELERATE}$ must define non-circular arcs. Noncircular gears designed using a sinusoidal function to define the acceleration and deceleration transitions have been found in practice to give good results. The equation defining the shape of the transitional part of the noncircular gears is:

$$\eta_{ACCELERATION} = A - B \cos C\theta \quad \text{(Eqn. 13)}$$

where $\eta_{ACCELERATION}$ is the gear ratio as a function of angular position during the transition, and $$A = (Y_1 + Y_2)/2 \quad \text{(Eqn. 14)}$$

$$B = (Y_2 - Y_1)/2 \quad \text{(Eqn. 15)}$$

$$C = 2\pi/\theta_{ACCELERATION} \text{ for the input gear} \quad \text{(Eqn. 16)}$$

The actual pitch line radius, $\rho$, for each noncircular gear can be determined once a choice has been made for the center-to-center distance between the two gears. The gear radii are given by:

$$\rho_{DRIVEN\ GEAR} = D_{CENTER}/(1 + \rho_{ACCELERATE}) \quad \text{(Eqn. 17)}$$

$$= D_{CENTER} - \rho_{DRIVEN\ GEAR} \quad \text{(Eqn. 18)}$$

where $\rho_{DRIVEN\ GEAR}$=the radius of the noncircular driven gear, $\rho_{DRIVE\ GEAR}$=the radius of the non-circular drive gear, and D center=the desired or chosen center-to-center gear distance $D_{CC}$ in FIG. 7.

By computing the gear ratios at intervals along the transition using Equation 13 above, a smooth curve defining the pitch line can be derived using Equations 17 and 18. The resulting smooth curve of the pitch line is used to construct a gear blank which is then used to manufacture the noncircular gears.

Referring to FIG. 8, the overall drive train for the illustrated embodiment of the machine of the present invention is illustrated schematically. Drive system 1000 drives first speed matching roller 150 and drive system 1100 drives second speed matching roller 125. Drive system 1000 comprises non-circular drive gear 1002 and non-circular driven gear 1004. Non-circular drive gear 1002 is turned at constant angular velocity of machine line shaft 1010. The driven, or output non-circular gear 1004 drives a multiplying linkage made up of drive shaft 1012, gear 1018, gear 1022 and linking gear-belt 1026. Gear 1022 drives speed matching roller 150 by means of shaft 1030. As discussed above, the circumference of speed matching roller 150 may be any feasible integral multiple, n, of the area under the designed speed profile for speed matching roller 150. This value for n then becomes the gear ratio for gears 1022 and 1018. For example, if speed matching roller 150 completes five repeats per revolution, then n=5, and the gear ratio of gear 1022 to 1018 is 5:1.

In a similar fashion, drive system 1100 comprises non-circular drive gear 1006 and non-circular driven gear 1008. Non-circular drive gear 1006 is turned at the constant angular velocity of machine line shaft 1014. The driven, or output non-circular gear 1008 drives a multiplying linkage made up of drive shaft 1016, gear 1020, gear 1024, and linking gear-belt 1028. Gear 1024 drives speed matching roller 125 by means of shaft 1032. The gear ratio for gears 1024 and 1020 in the multiplying linkage is the value of n for speed matching roller 125. As discussed above, n is any integral multiple of the area under the speed profile curve for speed matching roller 125. As shown in the embodiment depicted in FIG. 8, speed matching roller 125 is shown having a circumference equal to three repeats per revolution. Correspondingly, the gear ratio of gear 1024 to 1020 is 3:1.

Having discussed the design and construction of non-circular gear sets for driving the speed matching rollers, the vacuum mechanisms for holding workpiece components 204 and 214 to their respective anvil and die cut rollers and respective speed matching rollers will now be described.

Figures 9, 10:
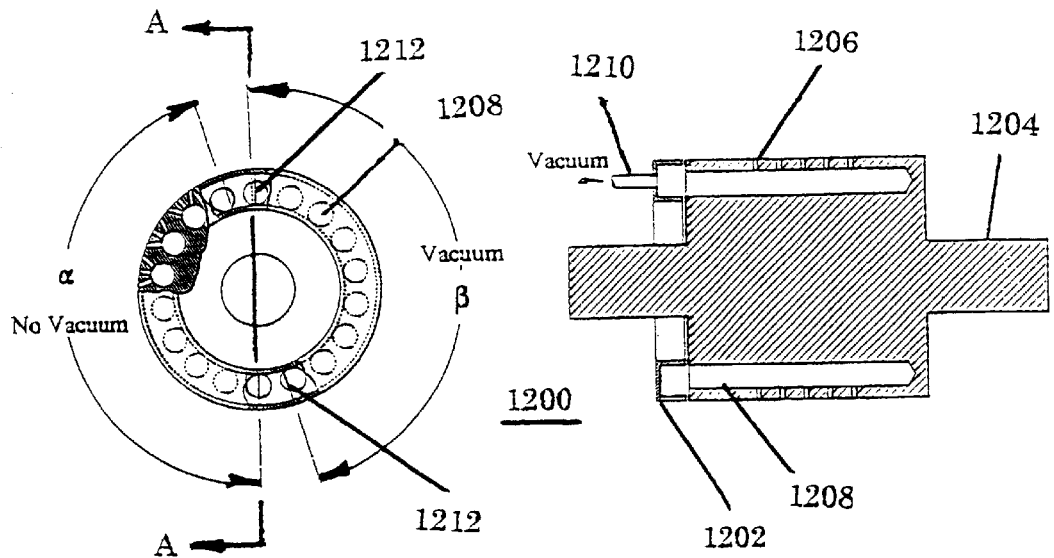
FIG. 9 shows a cross-sectional views of a side commutator vacuum system.
FIG. 10 shows a cross sectional view of the commutator of FIG. 9 taken along cut line AA.

Two conventional vacuum systems, well known in the art, may be used in the rollers of the machine of the invention, and are illustrated in FIGS. 9, 10, 11, and 12. FIG. 9 shows an end-view cross-section of a so-called "side-commutator" vacuum system 1200. FIG. 10 shows the vacuum system of FIG. 9 in a cross-section taken along cut line AA.

Referring to FIG. 10, the vacuum system comprises a stationary commutator 1202 and rotor 1204. The rotor 1204 has a series of tubular holes 1208 drilled into it, parallel to the axis of rotation of the rotor 1204. Holes 1206, drilled radially in the rotor 1204 connect the axial tubes or holes 1208 to the outer surface of the rotor 1204. Vacuum is introduced into the commutator through entry tube 1210 in the zone between the vacuum slugs 1212.

Referring to FIG. 9, vacuum slugs 1212 block the connection of the commutator 1202 to the axial tubes 1208 in the rotor 1204 during a fraction of each rotation of the rotor 1204. Thus, vacuum is introduced into tubes 1208 of the rotor 1204 only during that portion of each rotation of the rotor 1204 designated by the arc β when no vacuum slug 1212 is interposed between the commutator 1202 and the rotor 1204. The moveable vacuum slugs 1212 determine the ends of vacuum zone defined by the arc β. The lengths of the arcs α and β can be adjusted by appropriate placement of the vacuum slugs 1212. The side-commutator system 1200 is well adapted for rollers in the machine of the invention where it is necessary only to turn on and turn off vacuum as, for example in the die cut rollers 304 and 404.

Figures 11, 12:
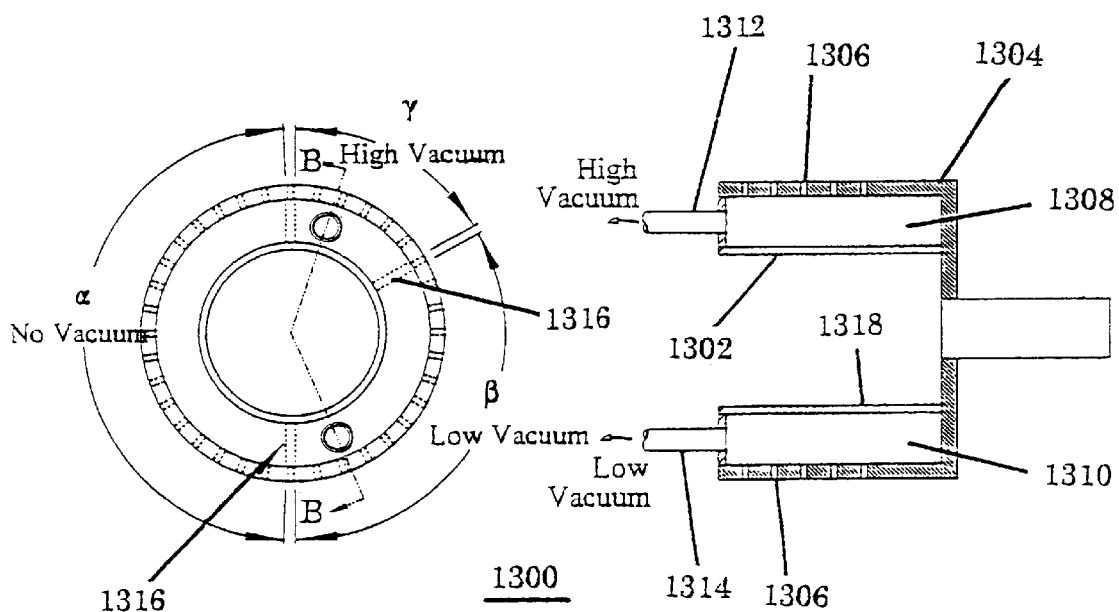
FIG. 11 shows a cross-sectional view of a center commutator vacuum system.
FIG. 12 shows a cross sectional view of the commutator of FIG. 11 taken along cut line BB.

FIG. 11 shows an end-view cross section of a so-called "center commutator" vacuum system 1300. FIG. 12 shows a cross-section of the system 1300 taken along the cut line BB.

Referring to FIG. 12, the system 1300 comprises a stationary commutator made up of two sections 1302 and 1318. The upper section in FIG. 12 comprises a chamber 1308 and tube 1312 through which high vacuum is introduced into chamber 1308. The lower section 1318 of the commutator in FIG. 12 comprises a chamber 1310 into which low vacuum is introduced through tube 1314.

Referring to FIG. 11, baffles 1316 are shown which divide the commutator into three chambers: a chamber into which no vacuum is introduced, a chamber of low vacuum, and a chamber of high vacuum. These chambers correspond to the arcs α, β, and γ, respectively. Unlike the side-commutator system described above, in the center commutator system, vacuum is maintained in the low and high vacuum chambers at all times, while the radial holes 1306 in concentric rotor 1304 move past each chamber. In this way, no vacuum, low vacuum, or high vacuum is introduced to the outer surface of the rotor 1304 sequentially as the rotor 1304 turns through each revolution. The lengths of arcs α, β, and γ, are determined, and can be changed by, movement of the baffles 1316. The center-commutator system 1300, with its capability of having zones of non vacuum, low vacuum, and high vacuum, is well adapted for rollers in the machine of the invention where it is necessary to turn on and turn off vacuum, and to have regions of high vacuum as, for example in the speed matching roller 150.

While there has been shown and illustrated one embodiment of the machine of the invention for depositing and registering two workpiece components of differing length on one another and subsequently onto a constantly moving web of material, it will be readily seen by one of ordinary skill in the mechanical arts that the machine can be modified to introduce and register third, fourth, fifth, etc. workpiece components by simply introducing additional components of die cut and anvil rollers and speed matching roller assemblies either adjacent to speed matching roller 150 or into the machine downstream in the process from the corresponding elements shown. In this manner, the machine of the present invention provides an efficient and cost-effective device for manufacturing multi-component articles of manufacture where there is a need to "stack" up and register two or more workpiece components and subsequently deposit them with registration on a constantly moving web. The speed matching roller system of the invention, with its non-linear gear drive, provides a means for carrying out this operation with workpiece components of differing lengths.

The process for manufacturing an article of manufacture employing the machine of the invention will now be described by reference to drawing FIGS. 4 and 13.

Referring to FIG. 4, in the process of the invention, a web of a first material 212 passes between a first die cut roller 404 and a first anvil roller 402 to cut the web of first material into discrete first workpiece components 214 having a component length of L1 and a repeat length between the leading edge of one cut workpiece component and the leading edge of the next successive workpiece component of $L_{CR1}$. The web of first material, the first die cut roller and the first anvil roller are moving at a constant surface speed of $L_{CR1}$ per repeat. The discrete workpiece components cut from the web of first material are held to the surface of the first die cut roller by vacuum means while the scrap portions, not shown in FIG. 4, of the web of first material move away from the surface of the first die cut roller.

A discrete first workpiece component 214 in the train of successive components cut from the first web is transferred to a first speed matching roller 150 which is spaced apart from the first die cut roller by a gap X of at least the uncompressed thickness of the first web of material.

Figure 13:
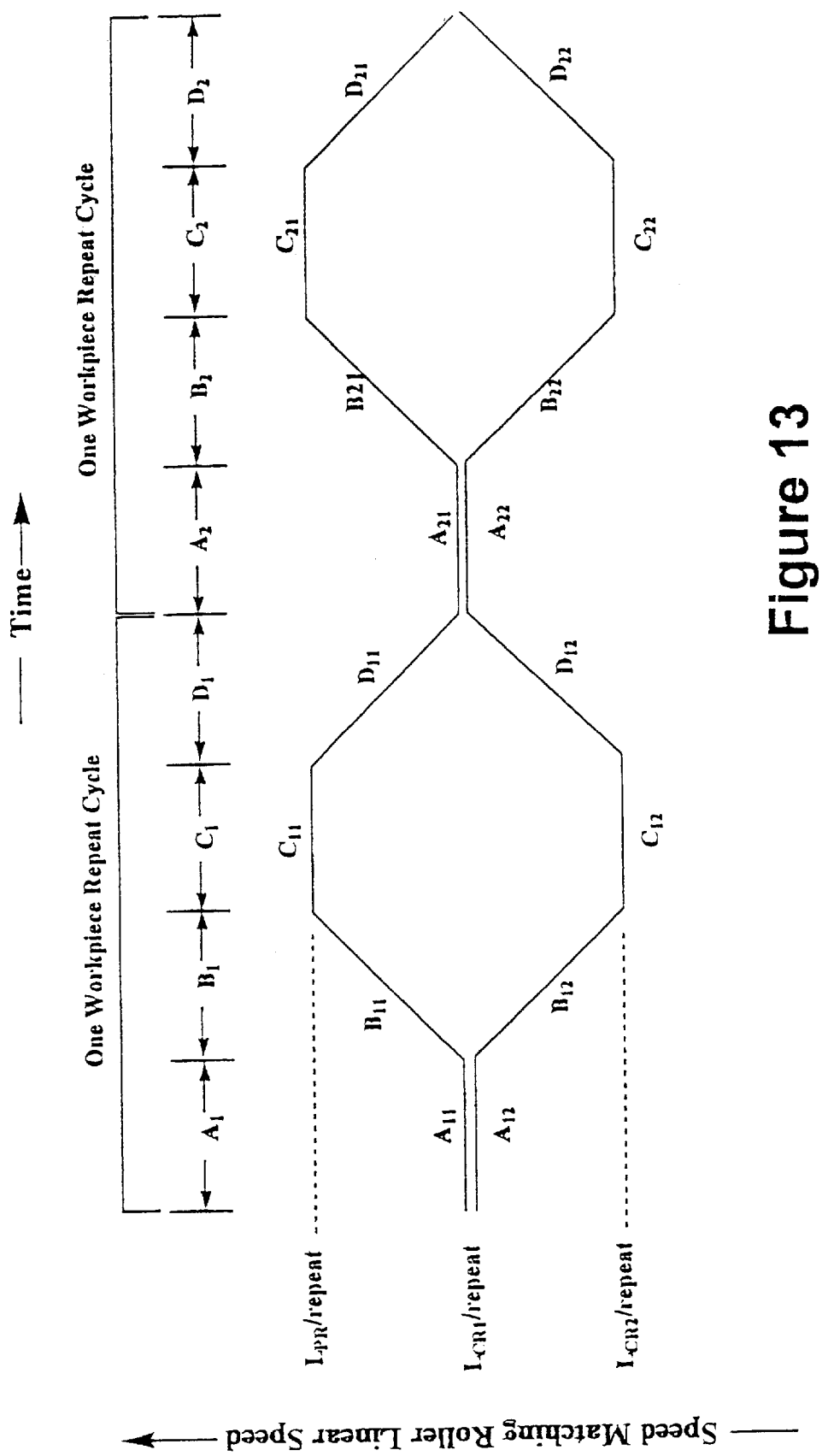
FIG. 13 shows a speed profile of the speed matching rollers of the machine of FIG. 1.

As the cut discrete first workpiece component enters the gap X between the first die cut roller 404 and the first speed matching roller 150, the first speed matching roller moves at a surface speed equal to $L_{CR1}$ per repeat for a dwell period $A_{11}$, preferably about one-fourth workpiece repeat cycle as shown in the speed profiles of the first and second speed matching rollers in FIG. 13. During this dwell period, a portion of the length of a first cut discrete workpiece component moves into the gap X separating the first die cut roller 404 and the first speed matching roller 150 and is transferred from the die cut roller 404 to the first speed matching roller 150. The transfer is effected by turning off the vacuum means holding the first cut discrete workpiece component 214 to the first die cut roller 404 and turning on vacuum to hold the leading fractional portion of the first discrete workpiece component 214 to the first speed matching roller 150.

Following the transfer of the leading portion of a first discrete workpiece component from the first die cut roller 404 to the first speed matching roller 150, the surface speed of the first speed matching roller 150 is accelerated during a period ($B_{11}$ in FIG. 13), again preferably about one-fourth workpiece repeat cycle, to a higher surface speed equal to the speed of a third web of product material 222, $L_{PR}$ per repeat where $L_{PR}$ is the distance between the leading edge of one product workpiece and the leading edge of the next following workpiece on the third product web of material.

As the first speed matching roller 150 is accelerated to its higher speed of $L_{PR}$ per repeat, the trailing portion of the first discrete workpiece component is pulled slideably off the slower moving surface of the first die cut roller 404, to which it is being lightly held by vacuum.

After accelerating, the first speed matching roller 150 then dwells at this higher surface speed, $L_{PR}$ per repeat, for a period of time, preferably about one-fourth workpiece repeat cycle ($C_{11}$ in FIG. 13). Since, in the embodiment shown, first speed matching roller 150 is of a circumference equal to a multiple number of product repeats, a previously cut and registered pair of first and second workpiece components 224 is entering gap W between the first speed matching roller 150 and the moving third web of product material 222. The registered first and second cut discrete workpiece components 224, held to the surface of the first speed matching roller 150, are transferred to the third web of moving product material 222 by turning off the vacuum holding the first and second cut discrete workpiece components 224 to the first speed matching roller 150. The action of the continuous vacuum holding the third web of product material to the surface over which it is passing, adheres the pair of components 224 to the moving web.

After the dwell period ($C_{11}$ in FIG. 13) at the higher linear surface speed of $L_{PR}$ per repeat, the first speed matching roller 150 decelerates during a period of time ($D_{11}$ in FIG. 13), preferably about one-fourth workpiece repeat cycle, to a surface speed of $L_{CR1}$ per repeat, and the cycle repeats.

As the first speed matching roller decelerates, the stacked, registered first and second cut discrete workpiece components 224, now resting on the moving third web of product material 222, are pulled slideably off the first speed matching roller to which they are lightly held by vacuum.

While the steps described above are occurring with regard to the first discrete workpiece components, simultaneously a web of a second material 202 passes between a second die cut roller 304 and a second anvil roller 302 to cut the web of second material 202 into discrete second workpiece components 204 having a component length of $L_{C2}$, with a repeat length between the leading edge of one cut workpiece component and the next successive workpiece component of $L_{CR2}$. The web of second material 202, the second die cut roller 304 and the second anvil roller 302 are moving at a constant surface speed of $L_{CR2}$ per repeat where $L_{CR2}$ is the distance between the leading edge of one of the second cut workpiece components and the leading edge of the next following second workpiece component as the components are being cut from the web of second material.

The discrete workpiece components 204 cut from the web of second material 202 are held to the surface of the second die cut roller 304 by vacuum means while the scrap portions of the web of second material move away from the surface of the second die cut roller.

The second die cut roller 304 and second speed matching roller 125 are spaced apart by a gap Y of at least the uncompressed thickness of the second web 202 of material. The second speed matching roller 125 moves at a slower linear surface speed equal to $L_{CR2}$ per repeat for a dwell period ($C_{12}$ in FIG. 13), preferably about one-fourth workpiece repeat cycle, sufficient to advance a cut discrete workpiece component 204 through the gap Y separating the second die cut roller 304 and the second speed matching roller 125. A prior cut workpiece component in the train of successive components cut from the second web of material is simultaneously moving through the gap Z between the second speed matching roller 125 and the first speed matching roller 150. The transfer is effected by turning off the vacuum means holding the second cut discrete workpiece component to the second die cut roller and turning on the vacuum to hold the leading fractional portion of the second discrete workpiece component to the second speed matching roller.

Following the transfer of the leading fractional portion of second discrete workpiece component from the second die cut roller 304 to the second speed matching roller 125, the linear surface speed of the second speed matching roller is accelerated during a period ($D_{12}$ in FIG. 13), again preferably about one-fourth workpiece repeat cycle, to a higher linear surface speed equal to the slower speed of the first speed matching roller, i.e. $L_{CR1}$ per repeat. During this period of acceleration, the second discrete workpiece component is pulled slideably off the surface of the second die cut roller to which it is being lightly held by vacuum.

The second speed matching roller 125 then dwells at this higher linear surface speed, $L_{CR1}$ per repeat, for a period of time ($A_{22}$ in FIG. 13), preferably about one-fourth workpiece repeat cycle, sufficient to advance a portion of the length of a prior cut second discrete workpiece component through the gap between the second speed matching roller 125 and the first speed matching roller 150. The first and second speed matching rollers are separated by a gap Z at least equal to the combined uncompressed thickness of the webs of first and second materials 202 and 212.

As a second cut discrete workpiece component 204, held by vacuum to the second speed matching roller, enters the gap Z between the first and second speed matching rollers, it is transferred to the first speed matching roller 150 in such a manner to overlay a first cut discrete workpiece component 214 being held by vacuum to the first speed matching roller 150.

As the leading edge of a cut discrete first workpiece component enters the gap Z between the first speed matching roller 150 and the second speed matching roller 125, the leading edge of a second discrete workpiece component 214 also enters the gap Z between the first and second speed matching rollers. The desired offset, if any, between the advancing leading edges of the first and second discrete workpiece components is adjusted by differential means driving the first and/or second die cut rollers indicated as 405 and 305 in FIG. 8.

Transfer of the second discrete workpiece component 204 from the second speed matching roller 125 to the first speed matching roller 150 is effected by turning off the vacuum holding the second workpiece component 204 to the second speed matching roller 125 and turning on high vacuum on the first speed matching roller 150 which serves to continue holding the first cut discrete workpiece component 214 to the first speed matching roller 150 while also holding the second discrete workpiece component 204, overlying the first component 214, to the first speed matching roller 150.

After this dwell period ($A_{22}$ in FIG. 13) at its higher surface speed, the second speed matching roller 125 decelerates during a period of time ($B_{22}$ in FIG. 13), preferably about one-fourth workpiece repeat cycle, to the surface speed, $L_{CR2}$ per repeat. As the second speed matching roller 125 decelerates, the trailing portion of the second discrete workpiece component 204 is pulled slideably off the second speed matching roller 125 to which it is being lightly held by vacuum.

A web 222 of a third material is transported on an endless belt 106 moving at a constant speed of $L_{PR}$ per repeat and is held to the endless belt by vacuum means. The endless belt 106 is separated from the first speed matching roller 150 by a gap W of at least the combined thickness of the uncompressed web of materials 202, 212, and 222. As the leading edges of the stacked first and second workpiece components 224 move into the gap W between the first speed matching roller 150 and the endless belt 106, the belt and the first speed matching roller are turning at the same surface speed of $L_{PR}$ per repeat. The first speed matching roller 150 speed dwells at this higher constant speed of $L_{PR}$ per repeat for a period, preferably about ¼ workpiece repeat cycle, to move a portion of the lengths of the stacked workpiece components through the gap W separating the first speed matching roller and the endless belt. As the leading edges of the stacked workpiece components enter the gap W, the high vacuum holding the stacked components 214 to the first speed matching roller 150 is turned off. As the first speed matching roller 150 then decelerates to its slower speed of $L_{CR1}$ per repeat, the faster moving endless belt 106, holding the stacked components to the third web 222 of moving material by vacuum means, pulls the stacked components 224 slideably off the first speed matching roller 150 and onto the web 222 of moving material. The overlying stacked first and second workpiece components, now held by vacuum and optional adhesive 112 to web 222 of the third material move down the process stream to subsequent operations.

Having thus described the process for cutting and stacking with registration two discrete workpiece components of different lengths and depositing them on a constantly moving web, the following example illustrates the use of the process and machine of the invention for the manufacture of a multi-layer feminine hygiene napkin.

EXAMPLE

Figure 14:
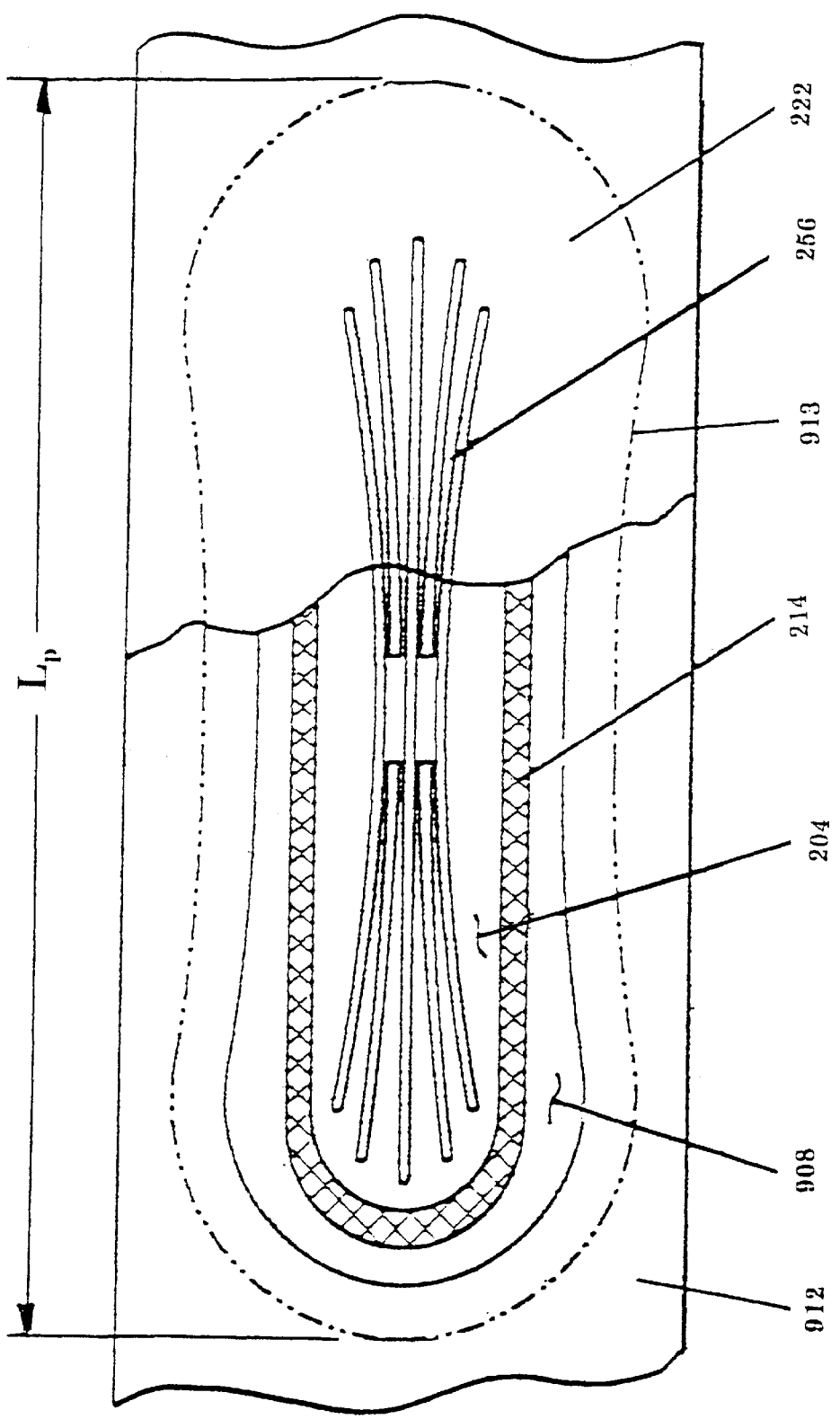
FIG. 14 shows in plan view the elements of an ultra-thin feminine napkin manufactured by the machine and process of the present invention.
Figure 15:
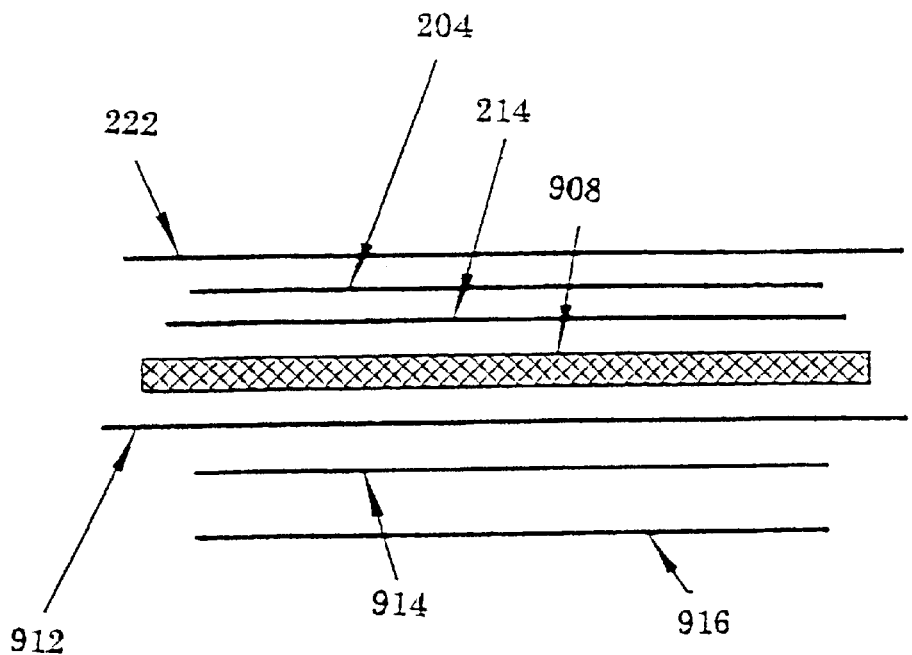
FIG. 15 shows in side cut-away view the elements of the ultra-thin feminine napkin of FIG. 14.
Figure 16:
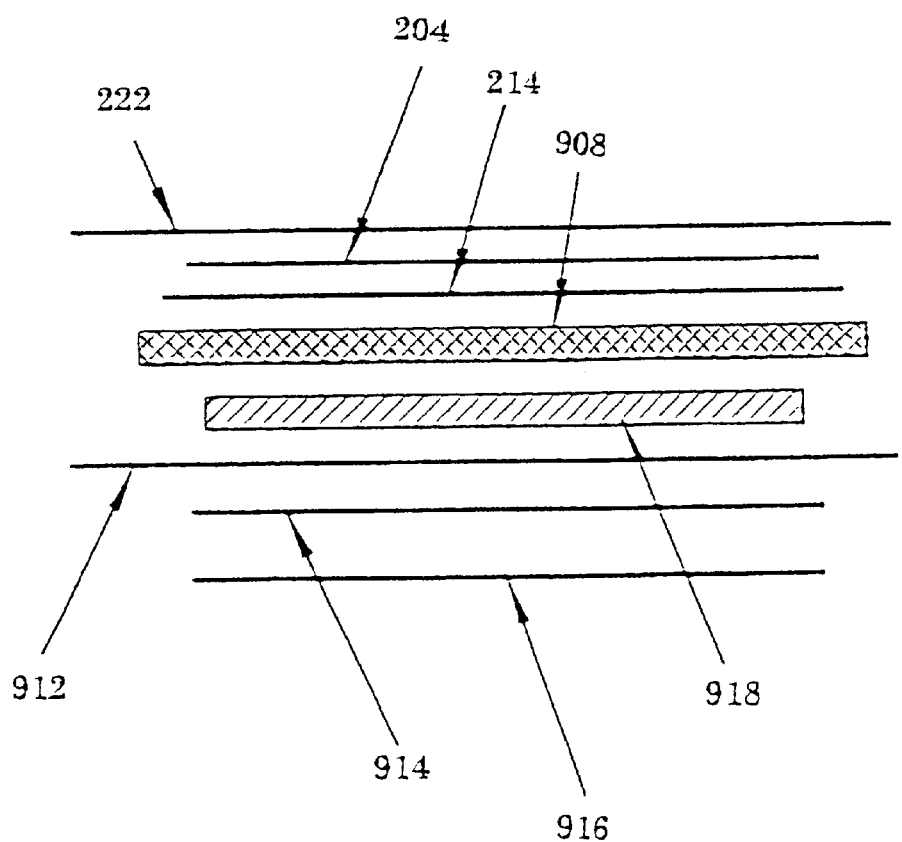
FIG. 16 shows in side cut-away view the elements of a "maxi-" feminine napkin.

A so-called ultrathin or "mini" napkin, suitable for use by a woman during days of light menstrual flow, is depicted schematically in plan view in FIG. 14 and in schematic side-view in FIG. 15. A thicker or so-called "maxi" napkin, suitable for use by a woman during days of higher menstrual flow, is depicted in schematic side view in FIG. 16. In FIG. 14, the elements of the napkin are shown in plan view, built up from the lowest "barrier component" to the uppermost "cover" component of the napkin. The cover component of the napkin is the component of the napkin worn closest to the user's body during use, and the barrier component is worn furthest from the user's body.

The napkin 900 depicted in FIG. 14 and described in this Example comprises a unique distribution feature which serves to disseminate, or distribute, body fluids prior to their reaching the absorbent component of the napkin in order to provide a more efficient napkin having longer service life prior to the need for its replacement and resulting greater comfort to the user. The distribution feature includes distribution and delay components not found in prior art napkins. The specific materials used for the various components of the napkin are described in detail in co-pending application Ser. No. 09/072172, filed May 5, 1998. the contents of which are incorporated herein by reference.

In this Example, specific lengths of the napkin and each component will be given to aid in understanding the invention. However, it is to be understood that the specific dimensions are cited merely for illustrative purposes and should not be read as limiting the scope of the invention as it is defined by the appended claims.

Figure 4A:
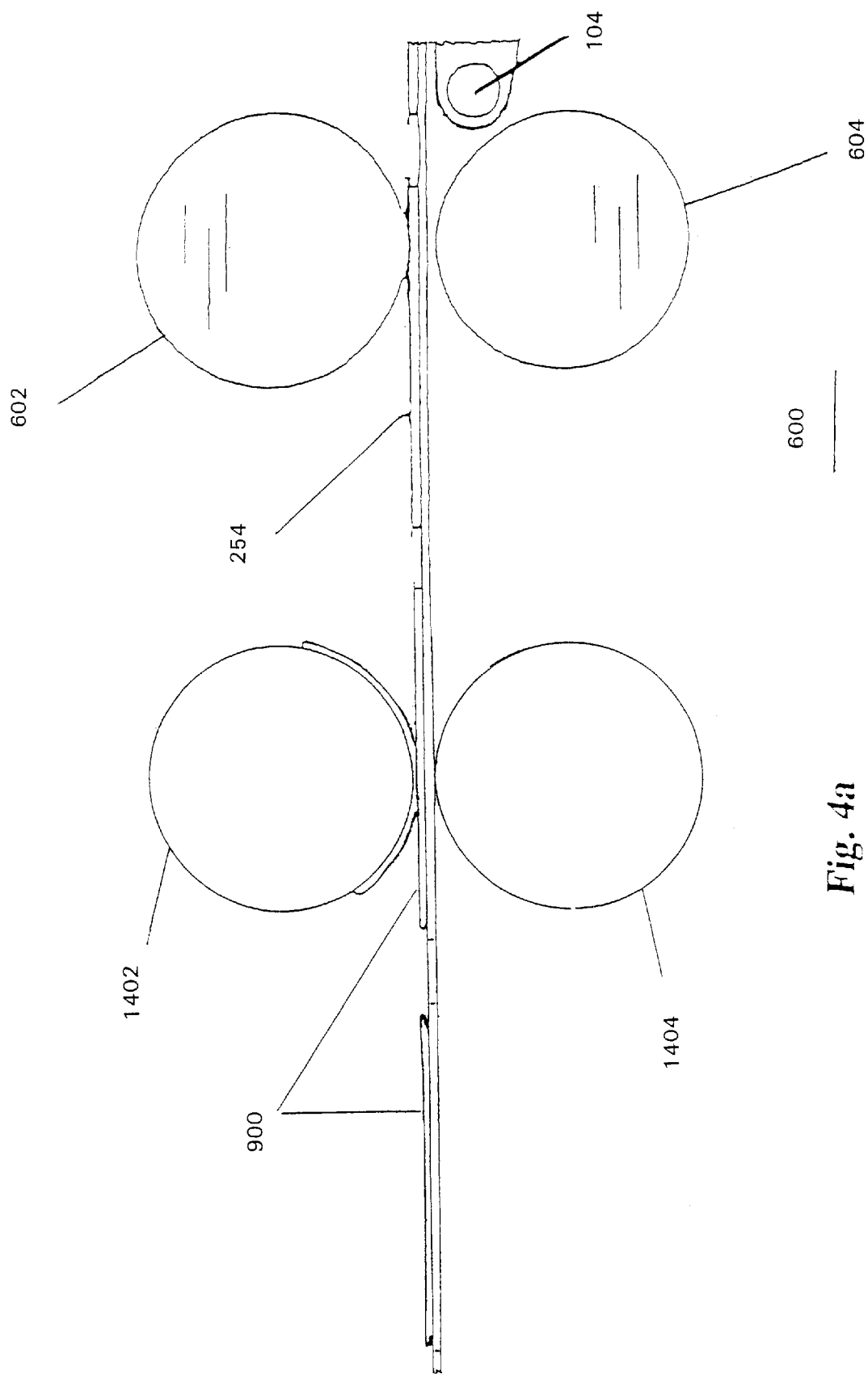

Referring to FIGS. 4, 4A, and 14, the napkin 900 has, when finally cut along dashed cut line 913, by cutting rolls 1402, 1404 shown in FIG. 4A, a dog-bone shape and an overall length $L_p$ equal to about 300 mm. With, for example, an allowance for in-process strain of 2 percent and a scrap of 0 mm between successive finished napkins when they are cut along dashed line 913, the product repeat length $L_{PR}$ is 306 mm. The napkin 900 comprises an upper cover 222 which is permeable to body fluids. Cover 222 constitutes the moving web of material 222 mentioned in the general process discussion above.

Directly under the cover 222 there is a distribution component 204 of length, $L_{C2}$, about 254 mm and component repeat length, $L_{CR2}$ of about 260 mm fabricated of a material which serves as a wicking agent to aid in the more or less uniform distribution of body fluids to the absorbent component below.

Directly under the distribution component 204 there is a transfer delay component 214 of length, $L_{C1}$, about 268 mm and component repeat length, $L_{CR1}$ of about 275 mm which is somewhat less permeable to body fluids than the cover layer 222. Transfer delay component 214 acts to slightly retard the flow of body fluids to permit the distribution component 204 above to effectively carry out its wicking function prior to the passage of body fluids through to the absorbent component below.

Using the exemplary lengths of each component just recited and referring to FIG. 1, the web 222 travels at a constant linear speed of 306 mm/repeat, which is the higher speed of first speed matching roller 150 in FIG. 1 and in the general process described above.

The web of first material 212 of FIG. 1, using the exemplary dimensions of this example, travels at a linear speed of 275 mm/repeat which is the surface speed of anvil and die cut rollers 402 and 404 and the slower speed of speed matching roller 150.

The web of second material 202, the anvil and die cut rollers 302 and 304 travel at a constant surface speed of 260 mm/repeat which is also the low constant dwell speed of speed matching roller 125.

These component dimensions and speed matching roller speeds are given in Tables 1 and 2, respectively.

TABLE 1

Component Lengths and Web Speeds

| Component | Reference Numeral | Component Length (mm) | Component Repeat Langth (mm) |
|---|---|---|---|
| Napkin | 900 | $L_P$ = 300 | $L_{PR}$ = 306 |
| Distribution component | 204 | $L_{C2}$ = 254 | $L_{CR2}$ = 260 |
| Transfer delay component | 214 | $L_{C1}$ = 268 | $L_{CR1}$ = 275 |

TABLE 2

Speed Matching Roller Speeds

| Speed Matching Roller | Constant Dwell Low Speed (mm/repeat) | Constant Dwell High Speed (mm/repeat) |
|---|---|---|
| 125 | 260 | 275 |
| 150 | 275 | 306 |

Referring again to FIG. 14, under the transfer delay component 214 there is the absorbent component 908. The barrier component 912, laying under the absorbent component 908, is typically made of a polymeric material which is not permeable to body fluids and which serves to shield the user's undergarments from staining by body fluids.

In the napkin 900 depicted in FIG. 14, the cover component is generally translucent and is typically made of a white material. To provide the consumer with visual cues that the napkin being purchased has the distribution feature mentioned above, the absorbent layer 908, transfer delay component 214 and distribution component 204 are fabricated of materials of different colors. For example, the absorbent component 908 and distribution component 204 may be white, while the transfer delay component 214 may be light blue, pink, peach, or some other pleasing color. The various components, viewed through the preferably translucent cover component 222 thus form a pleasing pattern. The cross-hatched region of the transfer delay component 214 in FIG. 14 appears as a uniform band of color through the translucent upper cover component 222. To add to the visual cues, the finished napkin 900 may be further embossed with a visual cue pattern 256.

It is highly desirable that the distribution component 204 and the transfer delay component 214 be carefully registered with respect to one another, and with the optional embossed visual cue 256. If the distribution component 204 and transfer delay component 214 are mismatched, the colored band is seen as a non-uniform band and detracts from the overall aesthetic appearance of the finished product. Moreover, if the optional embossed visual cue pattern 256 is similarly mismatched with the band of color, the overall pleasing appearance of the product is diminished.

Referring to the specific components with exemplary dimensions given above, the details of the general process for making the feminine napkin of this invention become clear with reference to FIG. 1.

A web of cover material 222 for the napkin 900 is fed to the machine of the invention at a constant speed of Lp per repeat or 306 mm/repeat. A web of first material 214 from which the transfer delay components 214 are cut is fed to the pair of die cut and anvil rollers 402 and 404 at a constant speed of $L_{CR1}$ per repeat, or 275 mm/repeat. A web 202 of second material is fed to anvil and die cut rollers 302 and 304 at a constant linear speed of $L_{CR2}$ per repeat, or 260 mm/repeat to be cut into distribution components 204.

The transfer delay 214 and distribution components 204 components are mated and registered by means of the speed transfer rollers 125 and 150 and transferred to the moving web of cover material 222. Speed matching rollers 125 and 150 repeatedly undergo acceleration to their respective higher constant dwell speeds of 275 mm/repeat and 306 mm/repeat, and deceleration to their respective low dwell speeds of 260 mm/repeat and 275 mm/repeat in a cyclical pattern which is 180° out of phase. By "180° out of phase" is meant that, as shown in FIG. 13, when speed matching roller 150 is moving at its highest dwell speed, roller 125 is moving at its lower dwell speed. Similarly speed matching roller 150 is moving at its lower dwell speed, roller 125 is moving at its higher dwell speed. In this manner, the components are controllably registered by mating them at a matched speed A spray or slot coat application of adhesive 112 is optionally made to the moving web of cover material, preferably in a pin-stripe pattern, to aid in holding the components to the web of cover material after they leave the region of vacuum. The adhesive also serves to hold the stacked distribution 204 and transfer delay 214 components to the web 222 of cover material and constantly moving web 106.

As shown in FIG. 1, embossing and anvil rollers 602 and 604 apply an optional embossed visual cue pattern 256 to the partially finished napkin. Downstream operations in the process, not shown, apply the barrier component 912, the light adhesive which serves to attach the napkin to a woman's undergarment, and the peel strip, all shown in FIGS. 15 and 16. In the "maxi" napkin shown in FIG. 16, a downstream operation in the process, also not shown, inserts an additional absorbent or superabsorbent pleget component 918 into the napkin prior to the addition of the barrier component 912, garment adhesive 914 and peel strip 916.

While there have been shown and exemplified preferred embodiments of the machine and process of the present invention, it will be clear to those skilled in the art that various departures may be made from the preferred embodiments of both the machine and process without departing from the scope of the invention as defined by the appended claims.

What is claimed is:

1. A method of manufacturing a multi-component absorbent personal hygiene article comprising a fluid permeable cover layer, a fluid distribution component contiguous to said cover layer, and a fluid transfer delay component contiguous to said fluid distribution component, the components being deposited on the cover layer, with the fluid distribution component, and the fluid transfer delay component being of different length and positionally registered with respect to one another; the method comprising:

a) cutting a fluid transfer delay component of length $L_{C1}$ and from a first moving web of material;

b) cutting a fluid distribution component of length $L_{C2}$ from a second moving web of material;

c) transferring the fluid transfer delay component (214) to a first speed matching roller (150) moving, for a portion of one revolution, at a first constant dwell speed equal to the speed of said first moving web of material (212);

d) transferring the fluid distribution component (204) to a second speed matching roller (125) moving, for a portion of one revolution, at a first constant dwell speed equal to the speed of said second moving web of material (202);

e) adjusting the speed of said second speed matching roller (125) bearing said fluid distribution component to move, for a portion of one revolution, at a second constant dwell speed matching that of the first constant dwell speed of said first speed matching roller (150);

f) transferring the fluid distribution component (204) from said second speed matching roller (125) to said first speed matching roller (150) during respective portions of the revolutions of the respective first and second speed matching rollers that the constant dwell speeds of said first and second speed matching rollers are matched, to overlay said fluid transfer delay component (214), and with registration of the fluid distribution component (204) over the respective said fluid transfer delay component (214), on said first speed matching roller (150), said fluid transfer delay component (214) thus underlying said fluid distribution component;

g) adjusting the speed of said first speed matching roller (150) bearing said fluid transfer delay component (214) underlying said fluid distribution component (204) to move at a second constant dwell speed, during a portion of one revolution of said first speed matching roller (150), matching that of a third moving web (222) of said cover layer material;

h) transferring the combination of said fluid transfer delay component (214) and said fluid distribution component (204) to said third moving web (222) of cover material during a portion of the revolution of said first speed matching roller (150) that the constant dwell speeds of said first speed matching roller (150) and said third web (222) of cover material are matched, to overlay, with registration, the combination of said fluid transfer delay component and said fluid distribution component, over said cover material thereby to make a web assembly; and i) cutting said web assembly and thereby forming a said multi-component absorbent personal hygiene article from said web assembly.

2. A method according to claim 1 wherein said cover layer is fabricated of a semi-transparent material.

3. A method according to claim 1 wherein said distribution component and fluid transfer delay component are fabricated of materials having independently selected colors.

4. A method according to claim 3 wherein said distribution component is of dimensions less than those of said fluid transfer delay component.

5. A method according to claim 1 where said distribution component is registered with respect to said fluid transfer delay component in such a manner that a uniform band of said fluid transfer delay component protrudes around the periphery of said fluid distribution component.

6. A method according to claim 1 wherein said cover layer is fabricated of a semi-transparent material and said distribution component and fluid transfer delay component, are fabricated materials having independently selected colors.

7. A method according to claim 6 where said distribution component is registered with respect to said fluid transfer delay component in such a manner that a uniform band of the color of said fluid transfer delay component is visible through said semi-transparent cover layer around the periphery of said fluid distribution component.

8. The method according to claim 1 further comprising the step of embossing said cover layer with a pattern.

9. The method according to claim 8 wherein said pattern of embossing is registered with respect to said fluid distribution and said fluid transfer delay components.

10. The method according to claim 9 wherein said pattern of embossing is centered with respect to said fluid distribution and said fluid transfer delay components.

11. A method of manufacturing a multi-component absorbent personal hygiene article comprising a semi-transparent fluid permeable cover layer, a fluid distribution component contiguous to said cover layer, and a fluid transfer delay component contiguous to said fluid distribution component, the components being deposited on the cover layer, with the fluid distribution component, and the fluid transfer delay component being of different length and positionally registered with respect to one another; the method comprising:

a) cutting a fluid transfer delay component from a first moving web of material having a first color;

b) cutting a fluid distribution component of dimensions less that those of said fluid transfer delay component from a second moving web of material having a second color;

c) transferring the fluid transfer delay component (214) to a first speed matching roller (150) moving, for a portion of one revolution, at a first constant dwell speed equal to the speed of said first moving web of material (212);

d) transferring the fluid distribution component (204) to a second speed matching roller (125) moving, for a portion of one revolution, at a first constant dwell speed equal to the speed of said second moving web of material (202);

e) adjusting the speed of said second speed matching roller (125) bearing said fluid distribution component to move, for a portion of one revolution, at a second constant dwell speed matching that of the first constant dwell speed of said first speed matching roller (150);

f) transferring the fluid distribution component (204) from said second speed matching roller (125) to said first speed matching roller (150) during respective portions of the revolutions of the respective first and second speed matching rollers that the constant dwell speeds of said first and second speed matching rollers are matched, to overlay said fluid transfer delay component (214), and with registration of the fluid distribution component (204) over the respective said fluid transfer delay component (214), on said first speed matching roller (150), said fluid transfer delay component (214) thus underlying said fluid distribution component;

g) adjusting the speed of said first speed matching roller (150) bearing said registered fluid transfer delay component (214) underlying said fluid distribution component (204) to move at a second constant dwell speed, during a portion of one revolution of said first speed matching roller (150), matching that of a third moving web (222) of said cover layer material;

h) transferring the combination of said fluid transfer delay component (214) and said fluid distribution component (204) to said third moving web (222) of cover material during a portion of the revolution of said first speed matching roller (150) that the constant dwell speeds of said first speed matching roller (150) and said third web (222) of cover material are matched, to overlay, with registration the combination of said fluid transfer delay component and said fluid distribution component, over said cover material thereby to make a web assembly; and i) cutting said web assembly and thereby forming a said multi-component absorbent personal care hygiene article from said web assembly, whereby a band of said first color of said fluid transfer delay component (214) is visible through said semi-transparent cover layer around the periphery of said fluid distribution component (204).

12. A method according to claim 11 wherein said fluid distribution component is registered with respect to said fluid transfer delay component to produce a symmetrical band of said first color of said fluid transfer delay component around the periphery of said fluid distribution component.

* * * * *